United States Patent
Woo et al.

(10) Patent No.: US 10,697,974 B2
(45) Date of Patent: Jun. 30, 2020

(54) METHODS AND COMPOSITIONS FOR PROTEIN IDENTIFICATION

(71) Applicant: President and Fellows of Harvard College, Cambridge, MA (US)

(72) Inventors: Sungwook Woo, Chestnut Hill, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/319,681

(22) PCT Filed: Jul. 21, 2017

(86) PCT No.: PCT/US2017/043206
§ 371 (c)(1),
(2) Date: Jan. 22, 2019

(87) PCT Pub. No.: WO2018/017914
PCT Pub. Date: Jan. 25, 2018

(65) Prior Publication Data
US 2019/0361031 A1 Nov. 28, 2019

Related U.S. Application Data

(60) Provisional application No. 62/365,493, filed on Jul. 22, 2016.

(51) Int. Cl.
*G01N 33/53* (2006.01)
*G01N 33/68* (2006.01)

(52) U.S. Cl.
CPC ..... *G01N 33/6818* (2013.01); *G01N 2458/10* (2013.01)

(58) Field of Classification Search
None
See application file for complete search history.

(56) References Cited

U.S. PATENT DOCUMENTS

2016/0046930 A1 2/2016 Emerick et al.
2017/0159136 A1* 6/2017 Church ............... C07H 21/02

FOREIGN PATENT DOCUMENTS

| WO | WO 2014/207245 A1 | 12/2014 |
| WO | WO-2016-007839 A1 * | 1/2016 |
| WO | WO 2016/123419 A1 | 8/2016 |
| WO | WO 2016/145416 A2 | 9/2016 |
| WO | WO 2017/143006 A1 | 8/2017 |
| WO | WO 2017/192633 A1 | 11/2017 |

OTHER PUBLICATIONS

Choi et al., Programmable in situ amplification for multiplexed imaging of mRNA expression. Nat Biotechnol. Nov. 2010;28(11):1208-12. Supp Info, 2 pages. Epub Oct. 31, 2010.
Harrow et al., Identifying protein-coding genes in genomic sequences. Genome Biol. 2009;10(1):201(1-8). Epub Jan. 30, 2009.
Neuman et al., Single-molecule force spectroscopy: optical tweezers, magnetic tweezers and atomic force microscopy. Nat Methods. Jun. 2008;5(6):491-505. Author Manuscript, 31 pages.
Yurke et al., A DNA-fuelled molecular machine made of DNA. Nature. Aug. 2000;406:605-8.
Zhang et al., Dynamic DNA nanotechnology using strand-displacement reactions. Nat Chem. Feb. 2011;3:103-13.
International Preliminary Report on Patentability dated Jan. 31, 2019, for Application No. PCT/US2017/043206.
Extended European Search Report dated Jan. 13, 2020, for Application No. EP 17831924.0.
Mendoza et al., Probing protein structure by amino acid-specific covalent labeling and mass spectrometry. Mass Spectrom Rev. Sep.-Oct. 2009;28(5):785-815. doi: 10.1002/mas.20203.
Zhou et al., Nanogold-based bio-bar codes for label-free immunosensing of proteins coupling with an in situ DNA-based hybridization chain reaction. Chem Commun (Camb). Dec. 28, 2012;48(100):12207-9. doi: 10.1039/c2cc36820j.

* cited by examiner

*Primary Examiner* — James Martinell
(74) *Attorney, Agent, or Firm* — Wolf, Greenfield & Sacks, P.C.

(57) ABSTRACT

Provided herein, in some embodiments, are methods and compositions for protein identification.

26 Claims, 10 Drawing Sheets

Specification includes a Sequence Listing.

Fig. 2
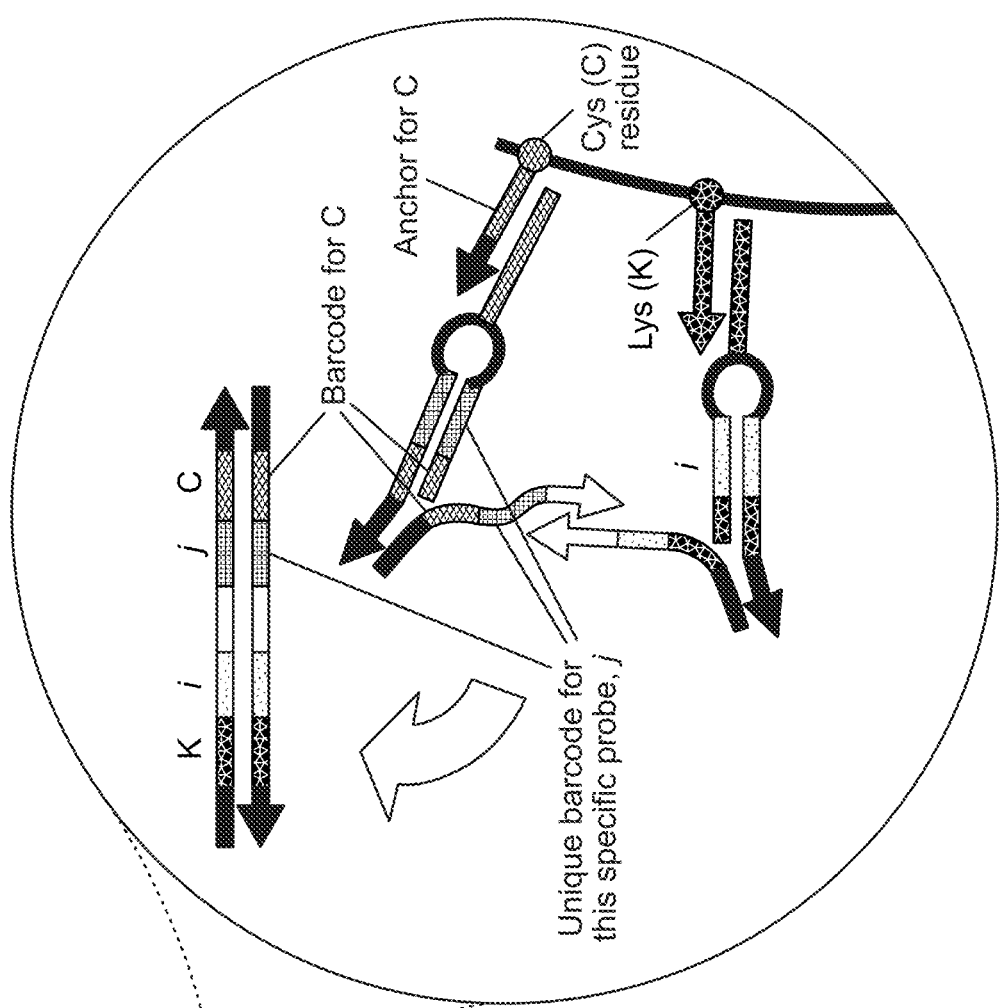
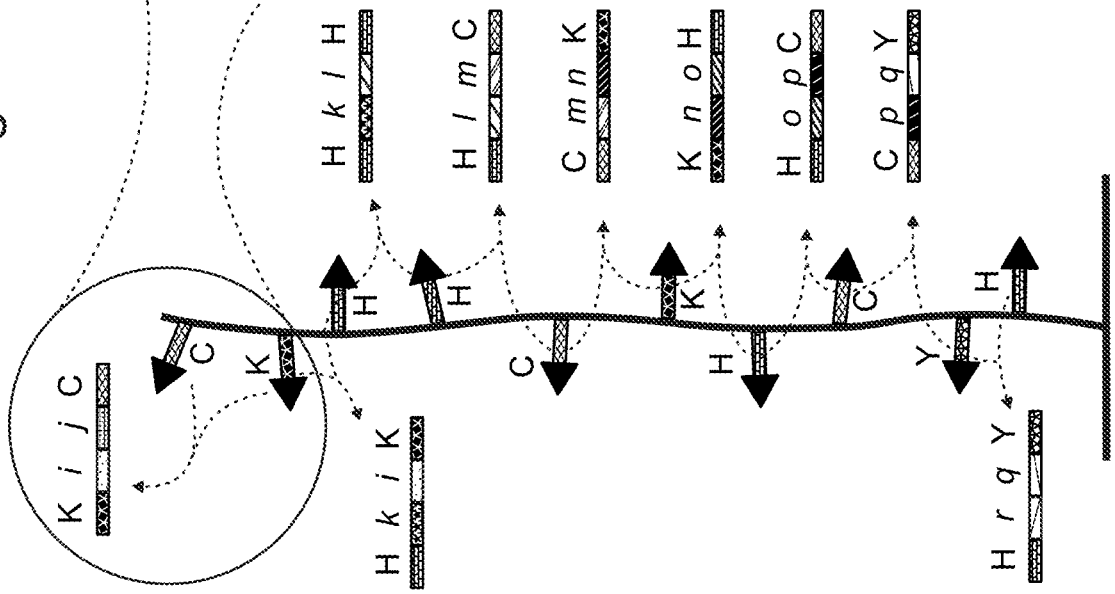

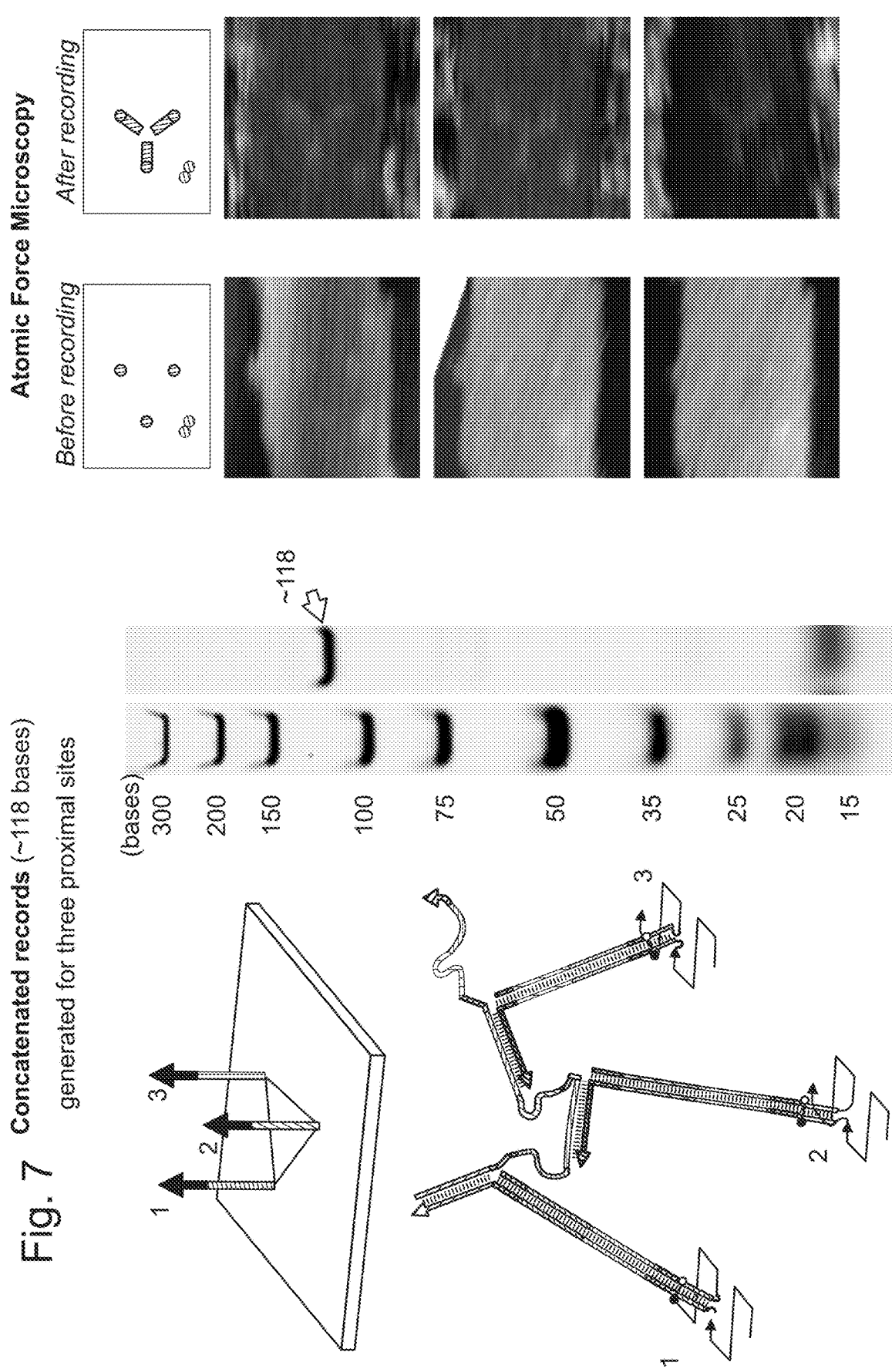
Fig. 7 Concatenated records (~118 bases) generated for three proximal sites United States Patent US 10,697,974 B2

METHODS AND COMPOSITIONS FOR PROTEIN IDENTIFICATION

RELATED APPLICATION

This application is a national stage filing under 35 U.S.C. § 371 of International Application Serial No. PCT/US2017/043206, filed Jul. 21, 2017, and claims the benefit under 35 U.S.C. § 119(e) of U.S. provisional application No. 62/365,493, filed Jul. 22, 2016, each of which is incorporated by reference herein in its entirety.

FEDERALLY SPONSORED RESEARCH

This invention was made with government support under Grant No. 5R01EB018659-02 awarded by National Institutes of Health. The government has certain rights in the invention.

BACKGROUND

Protein fingerprinting is traditionally an analytical technique for protein identification in which an unknown protein of interest is cleaved into smaller peptides, the absolute masses of which are measured using a mass spectrometer such as MALDI-TOF or ESI-TOF (Clauser K R et al. *Anal. Chem.* 1999; 71(14): 2871-82). This traditional method requires high purity and high abundance of the proteins of interest.

SUMMARY

Provided herein are systems, methods and compositions for identifying proteins by recording protein sequence information into nucleic acid records. Protein fingerprinting, as described herein, is based, at least in part, on the identification of individual protein molecules at the single-molecule level using molecular (e.g., nucleic acid) instruments that enable inspection and reconstruction of molecular landscapes. This technology is useful for transforming protein sequence information into nucleic acid sequence information, which can then be recorded and reported by the molecular instruments. For example, this technology may be used for proteomics research, where the identification of multiple proteins in protein expression mixtures, or identification of protein complexes in a high-throughput and multiplexed manner, is desired. Thus, the present technology may also be used in the pharmaceutical industry for analyzing disease models and patient samples as well as for drug screening, for example.

This technology provided herein provides a paradigm shift from traditional methods in proteomics research, where the current standard is based on mass spectrometry (MS) of fragmented peptides of proteins of interest. MS-based methods are inherently ensemble assays and, thus, require high purity and high abundance of the proteins of interest. By contrast, the technology provided herein represents an unprecedented "molecular swarm" technology where individual nucleic acid molecules record and report protein information, enabling paralleled and multiplexed, single-molecule level detection and analysis. Unlike traditional proteomics methods based on mass spectrometry, the protein identification methods provided herein provide faster acquisition of finer-resolution data, without the need of high purity or high abundance of protein samples.

Some aspects of the present disclosure provide methods that comprise combining in reaction buffer comprising a polymerase having strand displacement activity (a) a substrate to which a protein chain comprising amino acids labeled with barcoded DNA strands is attached, and (b) barcoded molecular instruments that bind to the DNA strands and produce nucleic acid records of the barcoded DNA strands, and incubating the reaction mixture under conditions that result in nucleic acid polymerization, strand displacement and annealing, for a time sufficient to produce the nucleic acid records.

In some embodiments, the methods further comprise collecting the nucleic acid records. In some embodiments, the methods further comprise sequencing the nucleic acid records and reconstructing the amino acid sequences. In some embodiments, the methods further comprise comparing the reconstructed amino acid sequences to a database of known protein sequences or to a genome. In some embodiments, the methods further comprise identifying the protein of interest based on a comparison between the reconstructed amino acid sequences from the nucleic acid records to a database or library of known protein sequences or the genome (e.g., genetically-identified protein-coding sequences from whole genome sequencing).

Some aspects of the present disclosure provide methods that comprise attaching a protein to substrate, denaturing the protein, stretching the protein to form a protein chain having one end attached to the substrate and the other end not attached to the substrate, and chemically coupling, to amino acids of the protein chain, barcoded DNA strands, wherein each barcoded DNA strand uniquely identifies a type of amino acid, thereby forming a DNA-labeled protein chain.

Some aspects of the present disclosure provide methods that comprise combining in reaction buffer comprising a polymerase having strand displacement activity (a) a DNA-labeled protein chain, (b) at least two barcoded catalytic molecules, wherein each barcoded catalytic molecule comprises (i) an unpaired 3' toehold domain, (ii) a paired stem domain formed by intramolecular nucleotide base pairing between a 3' subdomain of the barcoded catalytic molecule and a 5' subdomain of the barcoded catalytic molecule, wherein the paired stem domain comprises a first barcode sequence that identifies a type of amino acid and a second barcode sequence that identifies the barcoded catalytic molecule (e.g., is less than 100% (e.g., less than 90%) identical to the first barcode sequence or any other barcode sequence on another barcoded catalytic molecule), (iii) a paired palindromic domain, and (iv) a loop domain linked to a DNA strand that is complementary to a barcoded DNA strand coupled to an amino acid of the protein chain, and (c) at least one primer, wherein the primer is complementary to and binds to the 3' toehold domain of the barcoded catalytic molecules of (b), thereby forming a reaction mixture, and incubating the reaction mixture under conditions that result in nucleic acid polymerization, strand displacement and annealing, for a time sufficient to produce a nucleic acid record.

Some aspects of the present disclosure provide methods that comprise combining in reaction buffer comprising a polymerase having strand displacement activity (a) a DNA-labeled protein chain, (b) an initial barcoded catalytic molecule comprising (i) an unpaired 3' toehold domain, (ii) a paired domain located 5' from the toehold domain that is formed by nucleotide base pairing between a displacement strand and a template strand containing the toehold domain, wherein the paired stem domain comprises a first barcode sequence that identifies a type of amino acid and a second barcode sequence that identifies the initial barcoded catalytic molecule (e.g., is less than 100% identical to the first barcode sequence or any other barcode sequence on another barcoded catalytic molecule), and (iii) a loop domain linked to a DNA strand that is complementary to a barcoded DNA strand coupled to an amino acid of the protein chain, (c) a second barcoded catalytic molecule comprising (i) an unpaired 3' toehold domain, (ii) a paired domain located 5' from the toehold domain that is formed by nucleotide base pairing between a displacement strand and a template strand containing the toehold domain, wherein the paired stem domain comprises a first barcode sequence that identifies a type of amino acid and a second barcode sequence that identifies the second barcoded catalytic molecule (e.g., is less than 100% identical to the first barcode sequence or any other barcode sequence on another barcoded catalytic molecule), and (iii) a loop domain linked to a DNA strand that is complementary to a barcoded DNA strand coupled to an amino acid of the protein chain, wherein the unpaired 3' toehold domain of the second nucleic acid molecule is complementary to the displacement strand of the initial nucleic acid molecule, and (d) a primer complementary to nucleotides located in the unpaired 3' toehold domain of the initial nucleic acid molecule, thereby forming a reaction mixture; and incubating the reaction mixture under conditions that result in nucleic acid polymerization, strand displacement and annealing, for a time sufficient to produce a nucleic acid record.

In some embodiments, the protein is attached to the surface using a N-terminal-specific chemical coupling method or a C-terminal-specific chemical coupling method.

In some embodiments, the protein is denatured using urea or sodium dodecyl sulfate.

In some embodiments, the protein is stretched by applying external forces to the protein.

In some embodiments, applying external forces includes attaching a magnetic bead to the end of the protein that is not attached to the substrate and applying a magnetic field to the magnetic bead. In some embodiments, applying external forces includes attaching an electrically-charged particle to the end of the protein that is not attached to the substrate and applying an electric field to the electrically-charged particle. In some embodiments, applying external forces includes attaching a magnetically or electrically neutral particle (e.g., plastic microparticles) to the end of the protein that is not attached to the substrate and applying a centrifugal force to the particle.

In some embodiments, the DNA strands that are modified with NHS-ester are chemically coupled to amine-based amino acids of the linear protein such as lysine.

Also provided herein are compositions comprising (a) a substrate to which a protein chain comprising amino acids labeled with barcoded DNA strands is attached, and (b) at least two barcoded catalytic molecules, wherein each barcoded catalytic molecule comprises (i) an unpaired 3' toehold domain, (ii) a paired stem domain formed by intramolecular nucleotide base pairing between a 3' subdomain of the barcoded catalytic molecule and a 5' subdomain of the barcoded catalytic molecule, wherein the paired stem domain comprises a first barcode sequence that identifies a type of amino acid and a second barcode sequence that identifies the barcoded catalytic molecule (e.g., is less than 100% identical to the first barcode sequence or any other barcode sequence on another barcoded catalytic molecule), (iii) a paired palindromic domain, and (iv) a loop domain linked to a DNA strand that is complementary to a barcoded DNA strand coupled to an amino acid of the protein chain.

In some embodiments, the composition further comprises (c) at least one primer, wherein the primer is complementary to and binds to the 3' toehold domain of the barcoded catalytic molecules of (b), thereby forming a reaction mixture.

In some embodiments, the composition further comprises strand-displacing polymerase.

Also provided herein are kits comprising (a) a substrate, and (b) at least two barcoded catalytic molecules, wherein each barcoded catalytic molecule comprises (i) an unpaired 3' toehold domain, (ii) a paired stem domain formed by intramolecular nucleotide base pairing between a 3' subdomain of the barcoded catalytic molecule and a 5' subdomain of the barcoded catalytic molecule, wherein the paired stem domain comprises a first barcode sequence that identifies a type of amino acid and a second barcode sequence that identifies the barcoded catalytic molecule (e.g., is less than 100% identical to the first barcode sequence or any other barcode sequence on another barcoded catalytic molecule), (iii) a paired palindromic domain, and (iv) a loop domain linked to a DNA strand that is complementary to a barcoded DNA strand having a sequence that uniquely identifies a single amino acid.

In some embodiments, the kits further comprise barcoded DNA strands complementary to the loop domains of (b)(iv) and having a sequence that uniquely identifies a single amino acid.

The compositions and kits of the present disclosure may include any of the molecules and/or components described in any of the embodiments herein.

BRIEF DESCRIPTION OF THE DRAWINGS

FIG. 2 shows an example of a mechanism of encoding unique information for each amino acid site.

FIG. 7 shows data on the motion of a molecular motor system. FIG. 7 shows a schematic of the track design tested on a DNA nanostructure platform (left top image) and the molecular detail of the tracks after a motor has finished a recording reaction (left bottom image). FIG. 7, middle image, shows that after retrieval and PCR amplification, the records generated appear at the expected length range (118 nucletoides, nt) under denaturing gel electrophoresis. FIG. 7, right images, show an AFM visualization of the track sites and motors. Before adding motors, probe sites appear as dots; each probe is anchored by two loose single-stranded loops (typically 3 Ts), the sweeping of an AFM tip can only capture faint images of the track positions. Two dots in the bottom left corner are reference points. After the recording reaction, now that the track sites are connected and held together by the motor, they appear as a feature reminiscent of a tripod. The size of each origami rectangle is about 80 nm×100 nm. The schematic of the track design depicts concatenated records generated for three proximal sites (labeled 1, 2, and 3).

FIG. 8A shows a stem-anchored "upright" design, with the primer binding site at the farthest end of the probe. Linker, which connects to the target site, must be coupled to the probe at the bottom of the stem by, for example, click chemistry. This design may be used for a reach distance of about 30 nm. FIG. 8B shows an end-anchored "inverted" design, with the primer binding site at the bottom of the probe, next to the linker which connects to the target site. The linker can be part of the probe DNA strand, which makes the synthesis of the probe easier and more cost-effective. This inverted design allows for a shorter reach distance of about 5-10 nm. FIG. 8C shows a schematic diagram showing the reach distance between two adjacent probes with the upright design. This design may be used when a longer reach (~>30 nm) is desired and the reach is tunable by changing the lengths of the linker and/or barcode. FIG. 8D shows the reach distance between two adjacent probes with the inverted design. This design is may be used when a shorter reach (~5-10 nm) is desired and the reach is tunable in a similar manner to the upright designs.

DETAILED DESCRIPTION

Provided herein are protein "fingerprinting" methods that are used to identify individual protein molecules at the single-molecule level, enabled by the action of swarms of molecular instruments that inspect and report molecular landscapes. These molecular instruments are used to transform the sequence information of proteins into the sequence information of nucleic acids, which is used to reconstruct the protein sequences.

Protein Fingerprinting

Figure 1:
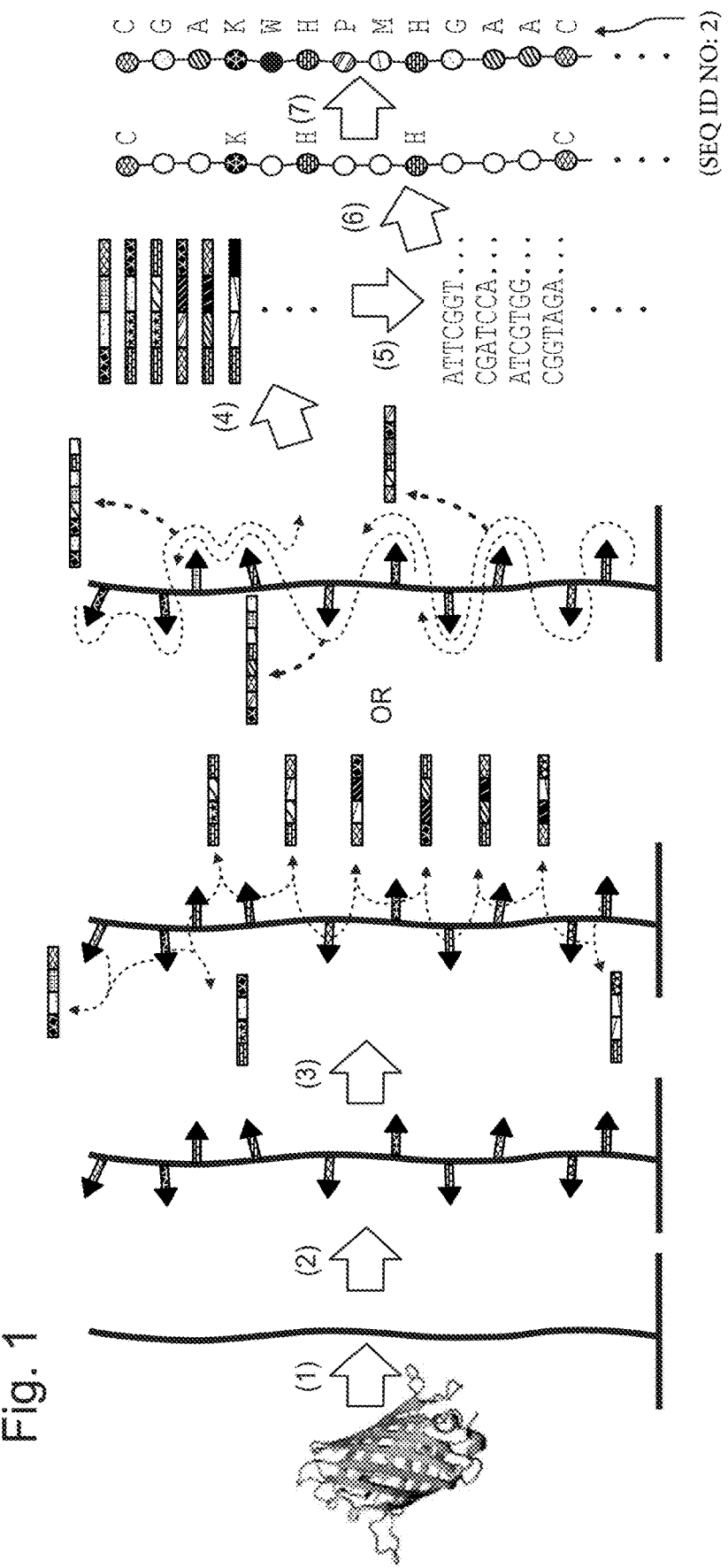
FIG. 1 shows an example of protein fingerprinting by molecular instruments.

A protein fingerprinting method of the present disclosure is described in FIG. 1. Proteins of interest are attached to a substrate (e.g., slide, plate or bead), denatured and stretched to form a protein chain (FIG. 1(1)). A subset of the amino acids of the protein chain (e.g., a protein without secondary structure) are then labeled ("barcoded") using short (e.g., 10-100 nucleotide) DNA strands containing a barcode nucleotide sequence that uniquely identifies a particular type of amino acid, as well as a unique molecular identifier (UMI, e.g., randomized sequence) (FIG. 1(2) and FIG. 2 inset). These "barcoded DNA strands" may also be referred to as "anchors" (see, e.g., FIG. 2). For the identification of proteins containing only natural amino acids, for example, twenty different barcoded DNA strands may be used, each barcoded DNA strand corresponding to, and thus uniquely identifying, an individual type of natural amino acid (e.g., alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y) or valine (V)). Each barcoded DNA strand bound to an amino acid encodes the identity of that particular amino acid.

DNA probes (molecular instruments, e.g., barcoded catalytic molecules, such as hairpin molecules and molecular motor systems, described below) are used to inspect the DNA-labeled amino acids and record the identity and proximity information of the amino acid (the barcoded DNA strand; FIG. 1(3)) as well as the identity information of each catalytic molecule. The recording may be performed using autocyclic proximity recording (APR) or molecular crawlers. Both methods are described below. Molecular instruments operate based on a principle that permits downstream molecular components to be synthesized in situ in a programmed fashion, copying the information from the target molecules (see, e.g., international application no. PCT/US2016/015503, filed Jan. 29, 2016, as well as in U.S. provisional application No. 62/296,310, filed Feb. 17, 2016, each of which is herein incorporated by reference in its entirety). Swarms of molecular instruments roam around the substrate to which protein molecules are attached and examine and report information from the molecular landscape in a massively parallel fashion. Multiple instruments can act on the same amino acid and generate partially redundant records. Nucleic acid records of the amino acid sequence information, generated by the molecular instruments, is then released and collected (FIG. 1(4)). Collected records are subsequently analyzed, for example, by next-generation sequencing (FIG. 1(5)). The redundant and partially overlapping sequence information from the nucleic acid records is used to reconstruct the sequence of the anchor-labeled amino acids (FIG. 1(6)). The DNA-labeled amino acids represent a subset of the full amino acid sequence of the protein of interest. This sub-sequence information is then compared and matched to a database or library of known protein sequences or the genome (e.g., genetically-identified protein-coding sequences from whole genome sequencing; Harrow et al., *Genome Biol.* 2009; 10:201), thus revealing the identity of the proteins of interest (FIG. 1(7)).

Attachment of proteins to a substrate (e.g., to a surface of a substrate) may be achieved, in some embodiments, using a N-terminal-specific chemical coupling method or a C-terminal-specific chemical coupling method. For example, site-specific cysteine residues at the termini (ends) of proteins can be immobilized on a surface of maleimide-modified, diamond-link, carbon-coated silicon (Ichihara et al., *J Proteome Res.* 2006; 5(9):2144-51). Click chemistry, including sequential Diels-Alder and zide-alkyne [3+2] cycloaddition reactions, can be used, in some embodiments, to immobilize proteins with an azide onto a solid surface (Sun et al., *Bioconjugate Chem.* 2006; 17(1): 52-7). Azides can be added via chemical modification of amino acid functional groups, for example (Soellner et al., *J Am Chem Soc.* 2003; 125: 11790-1). Further, an oligohistidine (His) segment may be genetically engineered to the N- or C-terminal of a protein, in some embodiments, resulting in specific chelation with metal ions (e.g., $Ni^{2+}$). Then, the $Ni^{2+}$ binds to an additional chelating agent, such as nitriloacetic acid (NTA), which is covalently bound to the immobilization surface (Kim D et al., *Biomicrofluidics* 2013; 7(4): 41501).

A substrate may be made of any material to which a protein can be attached. For example, a substrate may be a glass substrate, such as a glass slide, plate or bead. In some embodiments, a substrate is made of a plastic polymer (e.g., polystyrene or polypropylene). Other substrate materials are encompassed by the present disclosure.

Denaturation of surface-bound proteins may be achieved, in some embodiments, using denaturants, such as urea, sodium dodecyl sulfate, acetic acid, trichloroacetic acid, sulfosalicylic acid, sodium bicarbonate, ethanol, alcohol, formaldehyde, guanidium chloride or lithium perchlorate (Tanford, *Adv in Protein Chem.* 1968; 23:121-282; Myers, *Mol Life Sci.* 2014; 1-7). Other denaturation methods and reagents are encompassed by the present disclosure.

Protein stretching (e.g., to produce a substantially linear protein chain without secondary structure) may be achieved, in some embodiments, by applying external forces—mechanical, magnetic, centrifugal, or electric, for example. For example a magnetic bead may be attached to the end (N-terminus or C-terminus) of the protein that is not attached to a substrate, and a magnetic field may be applied to stretch the protein in a direction opposite the substrate. Likewise, an electrically-charged particle may be attached to the end of the protein that is not attached to a substrate, and an electric field may be applied to stretch the protein in a direction opposite the substrate. Centrifugation, atomic force microscopy (AFM), optical (laser) tweezers, microneedle manipulation, biomembrane force probing, or flow-induced stretching may also be applied to unfold the proteins into a substantially linear configuration (Neuman et al., *Nat Methods.* 2012: 5(6): 491-505). Other external forces may also be used.

Chemical coupling between barcoded DNA strands and amino acids may be achieved, in some embodiments, through amino acid-specific chemical modification methods. For example, lysine amino acids can be modified with N-hydroxysuccinimide (NHS)-ester chemistry (Goss et al., *J Chromatogr A.* 1990; 508:279), and cysteine residues can selectively interact with the maleimide group (Williams et al., *Curr Protoc Nucleic Acid Chem.* 2010; 4:41).

It should be understood that not every amino acid in a protein chain needs to be labeled with a DNA strand to ultimately to determine the identity of the protein. In some embodiments, at least 10% or at least 20% of the amino acids in a protein chain are labeled with barcoded DNA strands. For example, at least 15%, 20%, 25%, 30%, 35%, 40%, 45%, 50%, 55%, 60%, 65%, 70%, 75%, 80%, 85%, 90% or 95% of the amino acids in a protein chain may be labeled with barcoded DNA strands. In some embodiments, 10%-20%, 20%-30%, 20%-40%, 20%-50%, 20%-60%, 20%-70%, 20%-80%, 20%-90%, 20%-100%, 30%-40%, 30%-50%, 30%-60%, 30%-70%, 30%-80%, 30%-90%, 30%-100%, 40%-50%, 40%-60%, 40%-70%, 40%-80%, 40%-90%, 40%-100%, 50%-60%, 50%-70%, 50%-80%, 50%-90%, 50%-100%, 60%-70%, 60%-80%, 60%-90%, 60%-100%, 70%-80%, 80%-90% or 90%-100% of the amino acids in a protein chain are with barcoded DNA strands.

The length of a barcoded DNA strand and/or a DNA strand that is complementary to a barcoded DNA strand (e.g., a strand that is attached to a barcoded catalytic molecule) may vary. In some embodiments, the length of a barcoded DNA strand (or the barcode nucleotide sequence) is 10 to 100 nucleotides. For example, the length of a barcoded DNA strand (or the barcode nucleotide sequence) may be 10, 15, 20, 25, 30, 35, 40, 45, 50, 55, 60, 65, 70, 75, 80, 85, 90, 95 or 100 nucleotides. In some embodiments, the length of a barcoded DNA strand (or the barcode nucleotide sequence) is 10-100, 10-80, 10-80, 10-70, 10-60, 10-50, 20-100, 20-90, 20-80, 20-70, 20-60, 20-50, 30-100, 30-90, 30-80, 30-70, 30-60 or 30-50 nucleotides. In some embodiments, the length of a barcoded DNA strand (or the barcode nucleotide sequence) is longer than 100 nucleotides, while in other embodiments, the length of a barcoded DNA strand (or the barcode nucleotide sequence) is shorter than 10 nucleotides.

Barcoded DNA strands are used to "uniquely identify" a type of amino acid, which means that, in a single protein chain, for example, a single type of amino acid (e.g., lysine) is assigned a single barcode sequence (e.g., ATCGCTGACT (SEQ ID NO: 1)). Thus, as an example, every lysine that is labeled with a barcoded DNA strand (note that not every lysine needs to be labeled) in a protein chain is labeled with a barcoded DNA strand that includes the barcode sequence ATCGCTGACT (SEQ ID NO: 1).

A protein chain that comprises amino acids labeled with barcoded DNA strands is referred to as a "DNA-labeled protein chain." It should be understood that while each and every amino acid does not have to be labeled, any single amino acid should have only one label (one barcoded DNA strand).

Following preparation of a substrate comprising protein chains of interest, the substrate is combined with molecular instruments and associated primers, polymerase and dNTPs.

"Molecular instruments" for use herein are barcoded nucleic acid-based molecules (molecules made of primarily, or entirely, nucleic acid, e.g., DNA) that interact with (e.g., bind to) other molecules (e.g., other nucleic acids or proteins) and in so doing produce a nucleic acid record of that interaction (e.g., via nucleic acid elongation/polymerization reactions). That nucleic acid record may then be sequenced to provide amino acid sequence information about the protein of interest. Examples of molecular instruments for use in the protein fingerprinting methods of the present disclosure are described in international application no. PCT/US2016/015503, filed Jan. 29, 2016, as well as in U.S. provisional application No. 62/296,310, filed Feb. 17, 2016, each of which is herein incorporated by reference in its entirety).

A "primer" is a single-stranded nucleic acid that serves as a starting point for nucleic acid synthesis. A polymerase adds nucleotides to a primer to generate a new nucleic acid strand. Primers of the present disclosure are designed to be complementary to and to bind to the primer-binding domain (which may be a toehold domain) of a barcoded catalytic molecule, also referred to as a barcoded catalytic molecule. Thus, primer length and composition (e.g., nucleotide composition) depend, at least in part, on the length and composition of a primer-binding domain of a barcoded catalytic molecule. In some embodiments, a primer has a length of 4 to 40 nucleotides. For example, a primer may have a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, a primer may have a length of 4-10, 4-15, 4-20, 4-25, 4-30, 4-35, or 4-40 nucleotides.

Primers used in protein fingerprinting methods, in some embodiments, are used in combination with a strand-displacing polymerase. A "strand-displacing polymerase" refers to a polymerase that is capable of displacing downstream nucleic acid (e.g., DNA) encountered during nucleic acid synthesis. Different polymerases can have varying degrees of displacement activity. Examples of strand-displacing polymerases include, without limitation, Bst large fragment polymerase (e.g., New England Biolabs (NEB) # M0275), phi 29 polymerase (e.g., NEB # M0269), Deep VentR polymerase, Klenow fragment polymerase, and modified Taq polymerase. Other strand-displacing polymerases are encompassed herein.

Protein fingerprinting reactions may be performed under conditions that result in nucleic acid polymerization, strand displacement and annealing, for a time sufficient to produce a single-stranded or double-stranded nucleic acid record (elongated nucleic acid containing sequence information representative of individual molecular interactions). Such conditions may be, for example, physiological conditions (e.g., a temperature of 20-40 degrees Celsius, atmospheric pressure of 1, and/or a pH value of 6-8) but are not limited to physiological conditions.

A "reaction mixture" refers to a mixture of the components required to generate a nucleic acid record (e.g., a single-stranded or double-stranded nucleic acid record) from a DNA-labeled protein chain.

In some embodiments, a protein fingerprinting reaction is performed at a temperature of 20 to 60 degrees Celsius (° C.). For example, a protein fingerprinting reaction may be performed at a temperature of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., or 60° C.

In some embodiments, a protein fingerprinting reaction is performed for a time of 10 minutes (min) to 24 hours, or more. For example, a protein fingerprinting reaction may be performed for a time of 10 min to 3 hours (hr), 10 min to 12 hr, 10 min to 18 hr, or 10 min to 24 hr. In some embodiments, a protein fingerprinting reaction is performed for a time of 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min or 180 min.

A protein fingerprinting reaction mixture may, in some embodiments, have a salt concentration of 0.25-15 mM Mg and/or 50-250 mM Na.

A protein fingerprinting reaction mixture may, in some embodiments, have reaction dNTPs concentrations of 0.01-5 mM (e.g., 0.01 mM, 0.05 mM, 0.10 mM, 0.15 mM, 0.20 mM, 0.25 mM, 0.30 mM, 0.35 mM, 0.40 mM, 0.45 mM, 0.50 mM, 1.0 mM, 1.5 mM, 2.0 mM, 2.5 mM, 3.0 mM, 3.5 mM, 4.0 mM, 4.5 mM or 5.0 mM).

Buffers that may be used in a protein fingerprinting reaction include, without limitation, "Thermo-Pol Buffer" (New England Biolabs), phosphate buffered saline (with or without Mg or Na supplementation), any commercial or laboratory-prepared cell media, water or any pH-buffered solution supplemented with cationic salts sufficient for DNA hybridization and polymerase operation.

In some embodiments, the cycling rate of a protein fingerprinting reaction, as provided herein, is 1 full-record per 10 minutes per pair of barcoded catalytic molecules, but may be as rapid as 1 full record per second or as slow as 1 full record per 10 hours under certain (e.g., more restrictive) conditions.

At the end of a protein fingerprinting "cycle," nucleic acid records (referred to herein simply as "records") of the spatial configuration of amino acids within a protein chain or between different protein chains are produced (see, e.g., FIGS. 1 and 2). In some embodiments, the records are single-stranded. In some embodiments, the records are double-stranded. The length of the records may vary. For example, a record may have a length of 30 to 500 nucleotides (or nucleotide base pairs). In some embodiments, a record has a length of 30 to 100, 30 to 200, 30 to 300, 30 to 400, 50 to 100, 50 to 200, 50 to 300, 50 to 400 or 50 to 500 nucleotides (or nucleotide base pairs). In some embodiments, a record has a length of 80 to 100 nucleotides (or nucleotide base pairs), or 90 nucleotides (or nucleotide base pairs).

Records may be "released" from barcoded catalytic molecules via polymerase-mediated mechanisms or via spontaneous release of an extended primer from the primer-binding domain on a barcoded catalytic molecule.

After records are generated, they are collected and, in some embodiments, purified. For example, records may be collected in the supernatant of the reaction or by collecting all the contents of the reaction vessel. Further preparation of the records for sequencing may be sequencing platform-specific. Some platforms may require no further preparation, but in some embodiments, the records may have a combination of (1) a sequencing-specific 'adapter' or other oligonucleotides added to their ends, (2) undergo 'amplification' reactions (e.g., polymerase chain reaction (PCR)) in which identical or nearly-identical (e.g., 99%, 98%, 95%, 90%, 80% identical) copies of the records (with or without 'adapter' sequences) are produced, and (3) purification from other sequences, proteins, or reaction components that may interfere with preparation or sequencing. For example, adapter sequences may be ligated to the records using a common 'A-Tailing' technique, followed by gel electrophoresis purification, and finally PCR amplification. Alternatively, some embodiments allow for PCR amplification of records directly, possibly adding adapter sequences through long DNA primers, or followed by gel purification.

Collected nucleic acid records are then sequenced. In some embodiments, the records are sequenced using next-generation sequencing technologies. In some embodiments, Sanger sequencing is used as well as "post-next-generation sequencing" technologies under development, such as "nanopore-based" sequencing (e.g., Oxford Nanopore Technologies, nanoporetech.com). In a simplified system, for example, electrophoretic gels may be used to detect combinations of barcodes within a record by differentiating by the length of record produced, or standard resolution or super-resolution microscopy may be used to visually detect sequences of molecules by fluorescent in situ hybridization or similar approaches. Alternatively, nucleic acid microarrays (e.g., Agilent Technologies) may be used to detect records in a sequence-specific manner.

As discussed above, the anchor-labeled amino acids represent a subset of the full amino acid sequence of the target protein. This sub-sequence information is then compared and matched to a database or library of known protein sequences or the genome (e.g., genetically-identified protein-coding sequences from whole genome sequencing; see, e.g., Harrow et al., *Genome Biol.* 2009; 10:201), thus revealing the identity of the proteins of interest.

Molecular Instruments

The nucleic acid-based molecular instruments used herein enable the recordation and reconstruction of molecular landscapes. As discussed above, "molecular instruments" are nucleic acid-based molecules (molecules made of primarily nucleic acid, e.g., DNA) that interact with (e.g., bind to) other molecules (e.g., other nucleic acids or proteins) and in so doing produce a nucleic acid record of that interaction (e.g., via nucleic acid elongation/polymerization reactions). Examples of molecular instruments for use in the protein fingerprinting methods of the present disclosure are described in international application no. PCT/US2016/015503, filed Jan. 29, 2016, as well as in U.S. provisional application No. 62/296,310, filed Feb. 17, 2016, each of which is herein incorporated by reference in its entirety).

In some embodiments, autocyclic proximity reactions that include "barcoded catalytic molecules" are used to record and report protein sequence information. In other embodiments, reactions that convert chemical energy into mechanical work using "molecular motor molecules" are used to record and report protein sequence information.

Barcoded catalytic molecules of the present disclosure are typically attached to barcoded DNA strand that is complementary to a barcoded DNA strand that is attached to an amino acid of a protein chain. These barcoded DNA strands enable binding of a barcode catalytic molecule to an amino acid of a protein chain. In some embodiments, the barcoded DNA strand is attached to the single-stranded loop domain of a barcoded catalytic molecule (see, e.g., FIG. 2). In some embodiments, the barcoded DNA strand is attached to the single-stranded loop domain of a barcoded catalytic molecule through hybridization or "click chemistry." See, e.g., Kolb H. C., et al. *Angewandte Chemie International Edition* 2001, 40 (11): 2004-2021; and Evans R. A. *Australian Journal of Chemistry,* 2007, 60 (6): 384-395. In some embodiments, the barcoded DNA strand is attached to the single-stranded loop domain of a barcoded catalytic molecule through an intermediate molecule or chemistry. For example, an intermediate molecules may be biotin, antibodies, aptamers, nanobodies, nucleic acids, a drugs (e.g., small molecule drugs) and atoms (e.g., Li). Other molecules are encompassed herein.

Autocyclic Proximity Reaction Systems

In some embodiments, the molecular instruments used to record and report protein sequence information are referred to as barcoded catalytic molecules, which report proximity-based pairwise information through an "autocyclic proximity reaction (APR)." FIG. 2 shows an example of an autocyclic proximity reaction for recording and reporting protein sequence information. A specific amino acid (e.g., "Cys (C) residue") is labeled with a DNA strand containing a specific anchor sequence ("Anchor for C"). Barcoded catalytic molecules that bind to these anchors contain barcode sequences that indicate "C". Each barcoded catalytic molecule also contains a unique barcode sequence created by randomized sequences during synthesis of the molecules (see, FIG. 2, denoted by "i", "j", "k," etc.). Thus, all barcoded catalytic molecules binding to cysteine residues will contain the same barcode sequence for C; however, each barcoded catalytic molecule will also have an identifier sequence that is unique to each barcoded catalytic molecule. This enables identification of each molecular label from the records, thus enabling the mapping of the set of proximity information to specific locations in protein chains.

Figure 3:
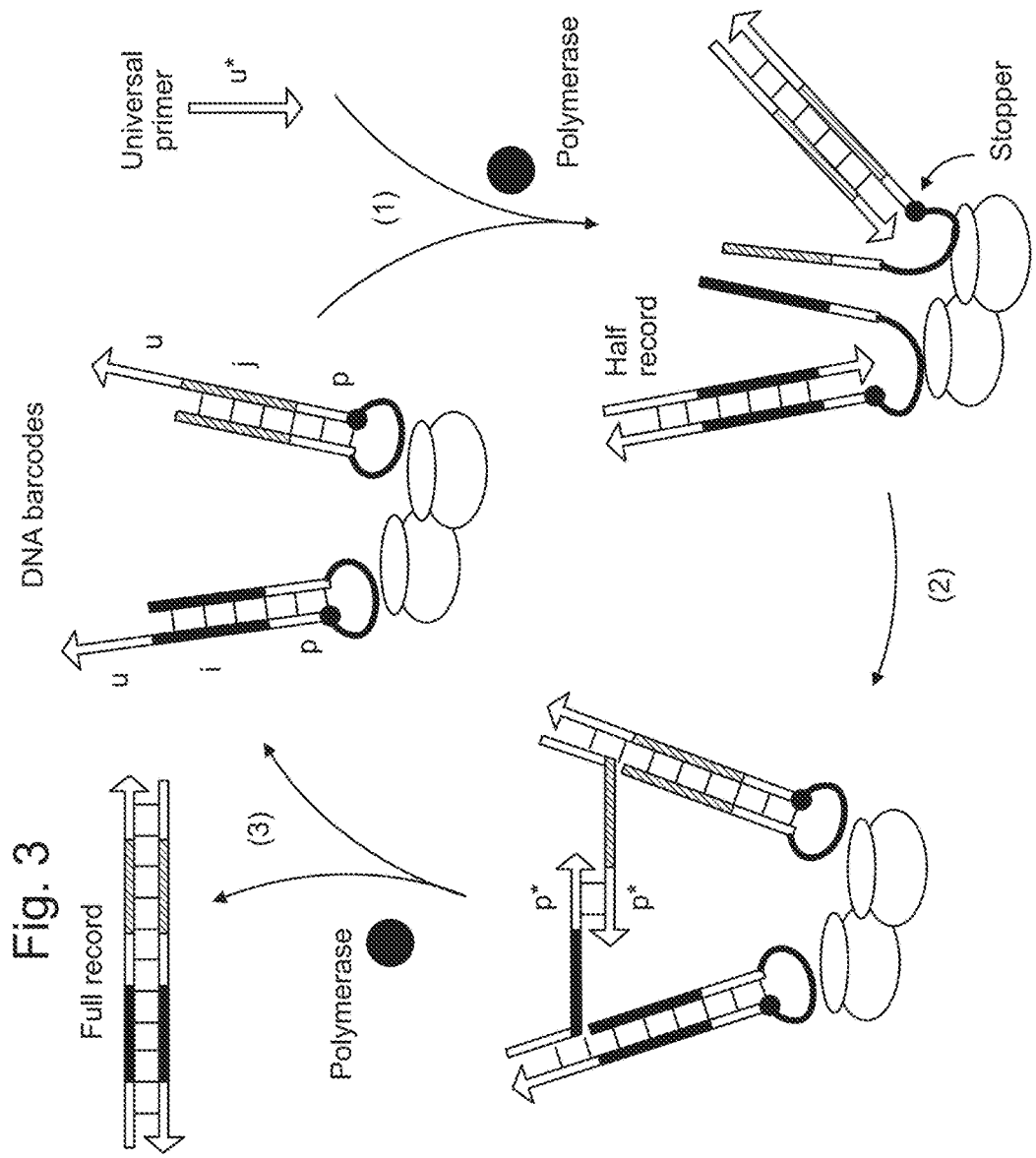
FIG. 3 shows a schematic of an example of an autocyclic proximity reaction (APR). An APR cycle, in this example, applies pairs of catalytic hairpins, with individual extension to bound primers generating half records (1), strand displacement and 3' palindromic domain hybridization (2), and half-record extension to full records (3).

FIG. 3 depicts in greater detail an example of a molecular mechanism underlying the barcoded catalytic molecules. In step (i), a soluble universal u* primer binds each barcoded catalytic molecule at a common single-stranded primer-binding u domain, and a displacing polymerase extends the primer through the barcode (i or j) domain and a palindromic p domain to a molecule or modification that terminates polymerization (e.g., a synthetic non-DNA linker), thereby generating a "half-record," which refers to a newly generated nucleic acid strand containing a universal u* primer, a barcode (i or j) and a palindromic p* sequence (e.g., u*-i*-p* or u*-j*-p*). Note that a letter with a superscript "*" denotes a sequence complementary to the sequence represented by the corresponding letter without the "*." In step (ii), half-records are partially displaced from the barcoded catalytic molecule by a "strand displacement" mechanism (see, e.g., Yurke et al., *Nature* 406: 605-608, 2000; and Zhang et al. *Nature Chemistry* 3: 103-113, 2011, each of which is incorporated by reference herein), and proximate half-records hybridize to each other through the 3' palindromic domains p*. In step (iii), the half-records are extended through the barcode (i and j) domains and primer-binding u domains, releasing soluble, full records that encode both barcoded (i and j) molecules. The barcoded catalytic molecules are "regenerated" and able to undergo additional cycles in the same or other molecular target pairings. Upon termination of the cycling reaction, records are collected, prepared, and sequenced by, for example, massively parallel next generation sequencing techniques.

"Strand displacement" refers to the mechanism by which two nucleic acid strands with identical sequences, when proximate to a single complementary nucleic acid strand (or segment of a strand), undergo relatively rapid (e.g., timescale <1 s) competition for that complement strand, 'displacing' each other from the complement presumably by a 'random-walk' mechanism.

Figure 4:
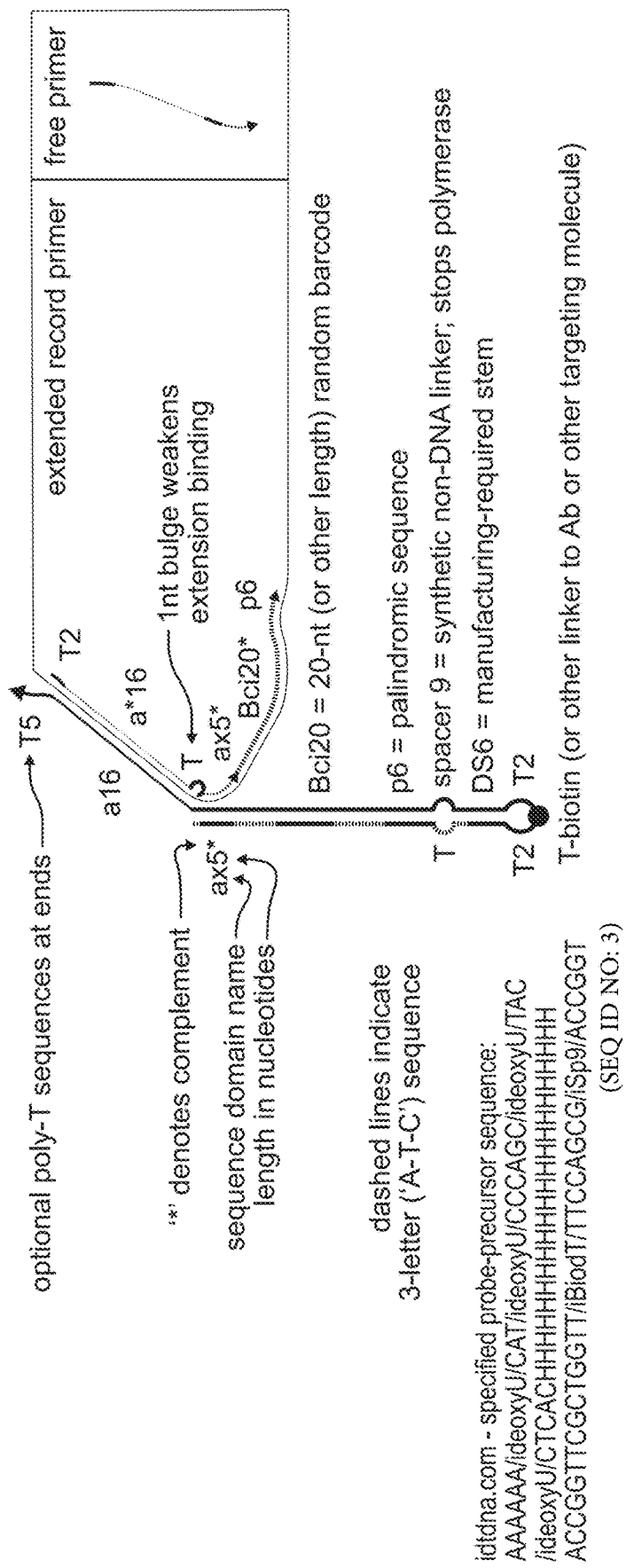
FIG. 4 shows an example of a catalytic hairpin molecule for use in accordance with the present disclosure (see, e.g., international application no. PCT/US2016/015503, filed Jan. 29, 2016, incorporated herein by reference in its entirety). The catalytic hairpin molecule comprises a T2 component, a T component, an ax5* component, a Bci20* component, and a p6 component.

Thus, a molecular instrument, as used herein, may be a barcoded catalytic molecule that comprises one or more nucleic acid strands arranged into a paired palindromic domain, a paired barcode domain, and a primer-binding domain. In some embodiments, the barcoded catalytic molecules are arranged to form a hairpin structure, which is a single stretch of contiguous nucleotides that folds and forms a paired domain, referred to as a "stem," and a single-stranded domain, referred to as a "loop." The paired domain is formed when nucleotides of two domains of the same nucleic acid base pair with each other (intramolecular base pairing). An example of a barcoded catalytic molecule is depicted in FIG. 4. It should be understand that barcoded catalytic molecules may not necessarily include a "loop." Other means (e.g., molecules) may be used to join together the ends of the paired domain where a loop would otherwise be located.

The length of a barcoded catalytic molecule may vary. In some embodiments, a barcoded catalytic molecule has a length of 25-300 nucleotides. For example, a barcoded catalytic molecule may have a length of 25-250, 25-200, 25-150, 25-100, 25-50, 50-300, 50-250, 50-200, 50-150 or 50-100 nucleotides. In some embodiments, a barcoded catalytic molecule has a length of 30-50, 40-60, 50-70, 60-80, 70-90, 80-100, 100-125, 100-150 or 100-200 nucleotides. In some embodiments, a barcoded catalytic molecule has a length of 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides. A barcoded catalytic molecule, in some embodiments, is longer than 300 nucleotides, or shorter than 25 nucleotides.

Barcoded catalytic molecules of the present disclosure, in some embodiments, comprise a two parallel nucleic acid strands (e.g., as two separate nucleic acids or as a contiguous folded hairpin). One of the strands is referred to as a "complementary strand," and the other strand is referred to as a "displacement strand." The complementary strand typically contains the primer-binding domain, or at least a single-stranded segment of the primer-binding domain, where the primer binds (e.g., hybridizes). The complementary strand and the displacement strand are bound to each other at least through a paired barcoded domain and through a paired palindromic domain. The "displacement strand" is the strand that is initially displaced by a newly-generated half-record, as described herein, and, in turn, displaces the newly-generated half-record as the displacement strand "rebinds" to the complementary strand.

Two nucleic acids or two nucleic acid domains are "complementary" to one another if they base-pair, or bind, to each other to form a paired nucleic acid molecule via Watson-Crick interactions (also referred to as hybridization). As used herein, "binding" refers to an association between at least two molecules due to, for example, electrostatic, hydrophobic, ionic and/or hydrogen-bond interactions under physiological conditions.

A "paired domain" of a nucleic acid refers to a domain of a nucleic acid (e.g., DNA or RNA) containing two parallel nucleic acid strands bound to each other by hydrogen bonds between complementary purines (e.g., adenine and guanine) and pyrimidines (e.g., thymine, cytosine and uracil), thereby forming a double helix. In some embodiments, the two parallel nucleic acid strands forming the paired domain are part of a contiguous nucleic acid strand. For example, as discussed above, methods of the present disclosure make use of barcoded catalytic molecules in the form of hairpin structures (e.g., FIG. 4).

A "single-stranded domain" of a nucleic acid refers to a domain of a nucleic acid containing a single nucleic acid strand, unbound to (unpaired with) a second nucleic acid strand. It should be understood that a barcoded catalytic molecule contains both a paired domain, referred to as the "stem," and a single-stranded domain (an unpaired domain), referred to as the "loop," as discussed above.

A "paired palindromic domain" refers to a domain of a barcoded catalytic molecule that is the same sequence of nucleotides whether read 5' (five-prime) to 3' (three prime) on one strand or 5' to 3' on the complementary strand with which it forms a double helix. For example, the following sequence, shown in FIG. 4, is considered a palindromic sequences: ACCGGT. Thus, a paired palindromic domain containing the foregoing sequence is arranged, as follows:

```
5'-ACCGGT-3'

3'-TGGCCA-5';
```

Palindromic sequences permit joining of barcoded catalytic molecules that are proximate to each other. Polymerase extension of a primer bound to the primer-binding domain produces a "half-record," which refers to the newly generated nucleic acid strand. Generation of the half record displaces one of the strands of the barcoded catalytic molecule, referred to as the "displacement strand." This displacement strand, in turn, displaces a portion of the half record (by binding to its "complementary strand"), starting at the 3' end, enabling the 3' end of the half record, containing the palindromic sequence, to bind to another half record similarly displaced from a proximate barcoded catalytic molecule.

In some embodiments, a paired palindromic domain has a length of 4 to 10 nucleotide base pairs. That is, in some embodiments, a paired palindromic domain may comprise 4 to 10 contiguous nucleotides bound to 4 to 10 respectively complementary nucleotides. For example, a paired palindromic domain may have a length of 4, 5, 6, 7, 8, 9 or 10 nucleotide base pairs. In some embodiments, a paired palindromic domain may have a length of 5 to 6 nucleotide base pairs. In some embodiments, the paired palindromic domain is longer than 10 nucleotide base pairs. For example, the paired palindromic domain may have a length of 4 to 50 nucleotide base pairs. In some embodiments, the paired palindromic domain has a length of 4 to 40, 4 to 30, or 4 to 20 nucleotide base pairs. In some embodiments, the palindromic domain may be replaced with an arbitrary sequence complementary to that produced by another barcoded catalytic molecule. In such embodiments, the barcoded catalytic molecules would be able to pair only with barcoded catalytic molecules having complementary 3' end sequences.

A paired palindromic domain may comprise guanine (G), cytosine (C), adenine (A) and/or thymine (T). In some embodiments, the percentage of G and C nucleotide base pairs (G/C) relative to A and T nucleotide base pairs (A/T) is greater than 50%. For example, the percentage of G/C relative to A/T of a paired palindromic domain may be 50% to 100%. In some embodiments, the percentage of G/C relative to A/T is greater than 60%, 65%, 70%, 75%, 80%, 85%, 90%, 95%.

In some embodiments, a paired palindromic domain may include an even number of nucleotide base pairs, although paired palindromic domain of the present disclosure are not so limited. For example, a paired palindromic domain may include 4, 6, 8 or 10 nucleotide base pairs. Alternatively, a paired palindromic domain may include 5, 7 or 9 nucleotide base pairs.

Among a plurality of barcoded catalytic molecules, typically, the paired palindromic domains are the same for each barcoded catalytic molecule of the plurality such that any two barcoded catalytic molecule proximate to each other are able to bind to each other through generated half-records containing the palindromic sequence. In some embodiments, however, the paired palindromic domains may be the same only among a subset of barcoded catalytic molecules of the plurality such that two different subsets contain two different paired palindromic domains.

A "paired barcoded domain" refers to a paired domain of a barcoded catalytic molecule that identifies the barcoded catalytic molecules as belonging to a particular amino acid. A paired barcoded domain may comprise any combination of nucleotides in random or rationally-designed order. In some embodiments, a paired barcoded domain has a length of 2 to 100 nucleotide base pairs. That is, in some embodiments, a paired barcoded domain may comprise 2 to 100 contiguous nucleotides bound to 2 to 100 respectively complementary nucleotides. For example, a paired barcoded domain may have a length of 2, 3, 4, 5, 6, 7, 8, 9, 10, 11, 12, 13, 14, 15, 16, 17, 18, 19 or 20 nucleotide base pairs. In some embodiments, a paired barcoded domain may have a length of 2 to 5, 2 to 10, 2 to 15, 2 to 20, 2 to 25, 2 to 30, 2 to 35, 2 to 40, 2 to 45, or 2 to 50 nucleotide base pairs. In some embodiments, a paired barcoded domain may have a length of 35 to 50, 35 to 60, 35 to70, 35 to 80, 35 to 90, or 35 to 100 nucleotide base pairs. In some embodiments, a paired barcoded domain is longer than 100 nucleotide base pairs. For example, a paired barcoded domain may have a length of 2 to 200 nucleotide base pairs. In some embodiments, a paired barcoded domain has a length of 2 to 190, 2 to 180, 2 to 170, 2 to 160, 2 to 150, 2 to 140, 2 to 130, 2 to 120, or 2 to 110 nucleotide base pairs.

A barcoded catalytic molecule is considered "unique" or "specific" to an amino acid if the barcoded domain of the barcoded catalytic molecule is associated only with that amino acid position and can be used to identify only that amino acid at its particular position in a protein chain.

A "primer-binding domain," which may be a "toehold domain," refers to a domain of a barcoded catalytic molecule where a single-stranded primer (e.g., DNA or RNA primer) binds to start replication. A primer-binding domain may be a single stranded domain or a partially double stranded domain, which refers to a domain containing both a single-stranded segment and a paired segment. An example of a partially paired primer-binding domain is shown in FIG. 4, where "a16" denotes a single-stranded segment of the primer-binding domain, and "ax5*" denotes a paired segment of the primer-binding domain. A primer-binding domain may comprise any combination of nucleotides in random or rationally-designed order. In some embodiments, a primer-binding domain has a length of 5-40 nucleotides (or nucleotide base pairs, or a combination of nucleotides and nucleotide base pairs, depending the single- and/or paired nature of the primer-binding domain). For example, a primer-binding domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a primer-binding domain has a length of 5, 10, 15, 20, 25, 30, 35 or 40 nucleotides. In some embodiments, a primer-binding domain has a length of 10, 11, 12, 13, 14, 15, 16, 17, 18, 19, 20, 21, 22, 23, 24 or 25 nucleotides. A primer-binding domain, in some embodiments, is longer than 40 nucleotides, or shorter than 5 nucleotides.

In some embodiments, a primer-binding domain is designed to accommodate binding of more than one (e.g., 2 or 3 different) primers.

With reference again to FIG. 4, as an example, extension of a primer (bound to a primer-binding site) by a displacing polymerase is typically terminated by the presence of a molecule or modification that terminates polymerization. Thus, in some embodiments, barcoded catalytic molecules of the present disclosure comprise a molecule or modification that terminates polymerization. A molecule or modification that terminates polymerization ("stopper" or "blocker") is typically located in a paired domain of a barcoded catalytic molecule, adjacent to the paired palindromic domain, such that polymerization terminates extension of the primer through the paired palindromic domain. For barcoded catalytic molecules arranged in the form of a hairpin, a molecule or modification that terminates polymerization may be located between the paired palindromic domain and the hairpin loop, as shown in FIG. 4 ("spacer 9"). In some embodiments, the molecule that terminate polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position.

In some embodiments, the efficiency of performance of a "stopper" or "blocker" modification be improved by lowering dNTP concentrations (e.g., from 200 μm) in a reaction to 100 μm, 10 μm, 1 μm, or less.

Inclusion of a molecule or modification that terminates polymerization often creates a "bulge" in a paired domain of a barcoded catalytic molecule (e.g., a stem domain for hairpin structures) because the molecule or modification is not paired (see, e.g., FIG. 4). Thus, in some embodiments, barcoded catalytic molecules are designed to include, opposite the molecule or modification, a single nucleotide (e.g., thymine), at least two of same nucleotide (e.g., a thymine dimer (TT) or trimer (TTT)), or an non-natural modification.

Thus, to prevent the polymerase from extending an end (e.g., a 5' or 3' end) of a barcoded catalytic molecule, a poly-T sequence (e.g., a sequence of 2, 3, 4, 5, 7, 8, 9 or 10 thymine nucleotides) may be used, as shown, for example, in FIG. 4. Alternatively, a synthetic base (e.g., an inverted dT) or other modification may be added to an end (e.g., a 5' or 3' end) of a barcoded catalytic molecule to prevent unwanted polymerization of the molecule. Other termination molecules (molecules that prevent extension of a 3' end not intended to be extended) include, without limitation, iso-dG and iso-dC or other unnatural nucleotides or modifications.

As discussed above, generation of a half record (see, e.g., FIG. 3A) displaces one of the strands of the barcoded catalytic molecule. This displaced strand, in turn, displaces a portion of the half record, starting at the 3' end. This displacement of the half-record is facilitated, in some embodiments, by a "paired displacement domain" adjacent to the molecule or modification that terminates polymerization (see, e.g., FIG. 4, "D56"). In embodiments wherein the barcoded catalytic molecule has a hairpin structure, the paired displacement domain may be located between the molecule or modification that terminates polymerization and the hairpin loop (see, e.g., FIG. 4). A paired displacement domain may comprise any combination of nucleotides in random or rationally-designed order. In some embodiments, a paired displacement domain has a length of 2 to 10 nucleotide base pairs. For example, a paired displacement domain may have a length of 2, 3, 4, 5, 6, 7, 8, 9 or 10 nucleotide base pairs. In some embodiments, a paired palindromic domain may have a length of 5 to 6 nucleotide base pairs. In some embodiments, a paired palindromic domain may contain only a combination of C and G nucleotides.

Displacement of the half-record may also be facilitated, in some embodiments, by modifying the reaction conditions. For example, some auto-cyclic reactions may include, instead of natural, soluble dNTPs for new strand generation, phosphorothioate nucleotides (2'-Deoxynucleoside Alpha-Thiol 2'-Deoxynucleoside Alpha-Thiol Triphosphate Set, Trilink Biotechnologies). These are less stable in hybridization that natural dNTPs, and result in a weakened interaction between half record and stem. They may be used in any combination (e.g., phosphorothioate A with natural T, C, and G bases, or other combinations or ratios of mixtures). Other such chemical modifications may be made to weaken the half record pairing and facilitate displacement.

Similarly, the barcoded catalytic molecule itself may be modified, in some embodiments, with unnatural nucleotides that serve instead to strengthen the hairpin stem. In such embodiments, the displacing polymerase that generates the half record can still open and copy the stem, but, during strand displacement, stem sequence re-hybridization is energetically favorable over half-record hybridization with stem template. Non-limiting examples of unnatural nucleotides include 5-methyl dC (5-methyl deoxycytidine; when substituted for dC, this molecule increase the melting temperature of nucleic acid by as much as 5° C. per nucleotide insertion), 2,6-diaminopurine (this molecule can increase the melting temperature by as much as 1-2° C. per insertion), Super T (5-hydroxybutynl-2'-deoxyuridine also increases melting temperature of nucleic acid), and/or locked nucleic acids (LNAs). They may occur in either or both strands of the hairpin stem.

In some embodiments, unnatural nucleotides may be used to introduce mismatches between new half record sequence and the stem. For example, if an isoG nucleotide existed in the template strand of the stem, a polymerase, in some cases, will mistakenly add one of the soluble nucleotides available to extend the half record, and in doing so create a 'bulge' between the new half record and the stem template strand, much like the bulge (included in the primer) of FIG. 4. It will serve the same purpose of weakening half-record-template interaction and encourage displacement.

In some embodiments, barcoded catalytic molecules of the present disclosure are arranged to form a hairpin structure, which is a single stretch of contiguous nucleotides that folds and forms a paired domain, referred to as a "stem," and a single-stranded domain, referred to as a "loop." In some embodiments, the single-stranded loop domain has a length of 3 to 50 nucleotides. For example, the single-stranded loop domain may have a length of 3, 4, 5, 6, 7, 8, 9 or 10 nucleotides. In some embodiments, the single-stranded loop domain has a length of 3 to 10, 3 to 15, 3 to 20, 3 to 25, 3 to 30, 3 to 35, 3 to 40, 3 to 45, or 3 to 50 nucleotides. In some embodiments, the single-stranded loop domain is longer than 50 nucleotides. For example, the single-stranded loop domain may have a length of 3 to 200 nucleotides. In some embodiments, the single-stranded loop domain has a length of 3 to 175, 3 to 150, 3 to 100, or 3 to 75 nucleotides. In some embodiments, a loop domain includes smaller domains of intramolecular base pairing. A hairpin loop, in some embodiments permits flexibility in the orientation of the barcoded catalytic molecule relative to a target binding-moiety. That is, the loop typically allows the barcoded catalytic molecule to occupy a variety of positions and angles with respect to the target-binding moiety, thereby permitting interactions with a multitude of nearby barcoded catalytic molecules (e.g., attached to other targets) in succession.

Barcoded catalytic molecules of the present disclosure may be DNA such as D-form DNA and L-form DNA and RNA, as well as various modifications thereof. Nucleic acid modifications include base modifications, sugar modifications, and backbone modifications. Examples of modified nucleic acids (e.g., DNA variants) that may be used in accordance with the present disclosure include, without limitation, L-DNA (the backbone enantiomer of DNA, known in the literature), peptide nucleic acids (PNA) bisPNA clamp, a pseudocomplementary PNA, locked nucleic acid (LNA), and co-nucleic acids of the above such as DNA-LNA co-nucleic acids. Thus, the present disclosure contemplates nanostructures that comprise DNA, RNA, LNA, PNA or combinations thereof. It is to be understood that the nucleic acids used in methods and compositions of the present disclosure may be homogeneous or heterogeneous in nature. As an example, nucleic acids may be completely DNA in nature or they may be comprised of DNA and non-DNA (e.g., LNA) monomers or sequences. Thus, any combination of nucleic acid elements may be used. The nucleic acid modification may render the nucleic acid more stable and/or less susceptible to degradation under certain conditions. For example, in some embodiments, nucleic acids are nuclease-resistant.

In some embodiments, a catalytic probe comprises a single-stranded nucleic acid containing, in the following 5' to 3' direction, a first domain, a second domain, an unpaired loop domain, a third domain, a fourth domain, and a fifth domain, wherein (a) the first and fourth domains are complementary to each other and contain a barcode sequence specific for a single amino acid (e.g., A, R, N, D, C, E, Q, G, H, I, L, K, M, F, P, S, T, W, Y or V), (b) the second and third domains are complementary to each other and contain a barcode sequence specific for the probe (to uniquely identify the probe), and (c) the unpaired loop domain is linked to an unpaired linker nucleic acid strand. See, e.g., FIG. 2. In some embodiments, provided herein is a composition comprising (a) a substrate to which a protein chain comprising amino acids labeled with barcoded DNA strands is attached and (b) at least 1 or at least 2 (e.g., at least 3, 4, 5, 6, 7, 8, 9, 10, 15 or 20) of the foregoing catalytic probes. In some embodiments, the unpaired linker nucleic acid strand comprises a nucleotide sequence complementary to a nucleotide sequence of a barcoded DNA strand (which labels a single amino acid of a protein) of the protein chain. In some embodiments, the composition further comprises at least one nucleic acid primer strand containing a sequence complementary to the fifth unpaired domain of the catalytic probe.

Barcoded Molecular Motor Systems

Figure 5:
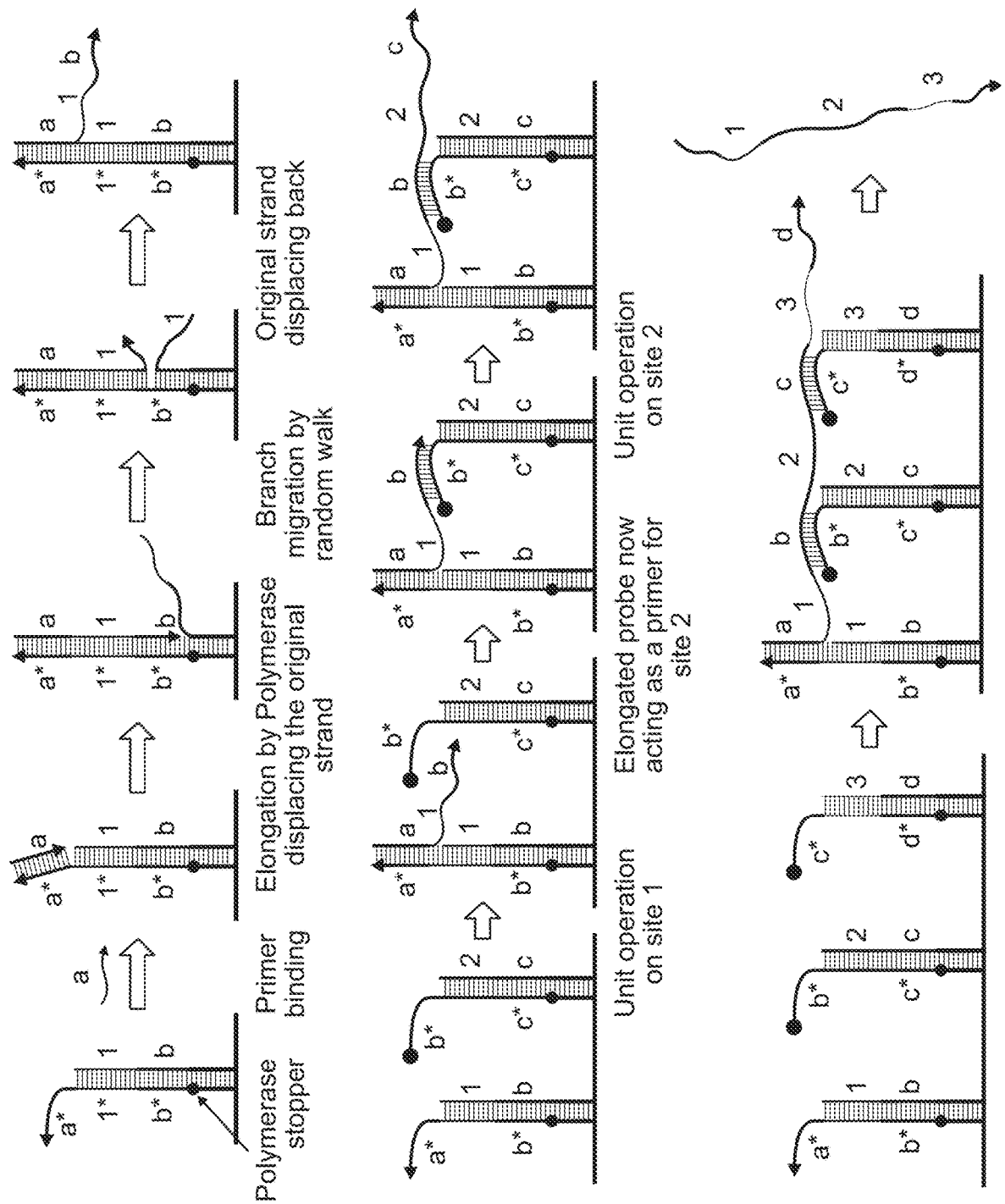
FIG. 5 shows a basic operation mechanism of an example of a molecular motor molecule (referred to as a "molecular crawler"). The top row depicts the unit operations on a single site. The middle row depicts one step of crawling between two neighboring sites. The bottom row depicts the initial and final states of three-site "track," where each site is a DNA-labeled amino acid in a protein chain of interest. The generated nucleic acid records can be released by multiple mechanisms. Circular arrowheads at the end of some strand species indicate modifications for protection against elongation by polymerases (e.g., inverted dT). The basic operation mechanism of the example comprises nucleic acid segments 'a', 'a*', 'b', 'b*', 'c', 'c*', 'd', 'd*', '1', '1*' '2', and '3'.
Figure 6:
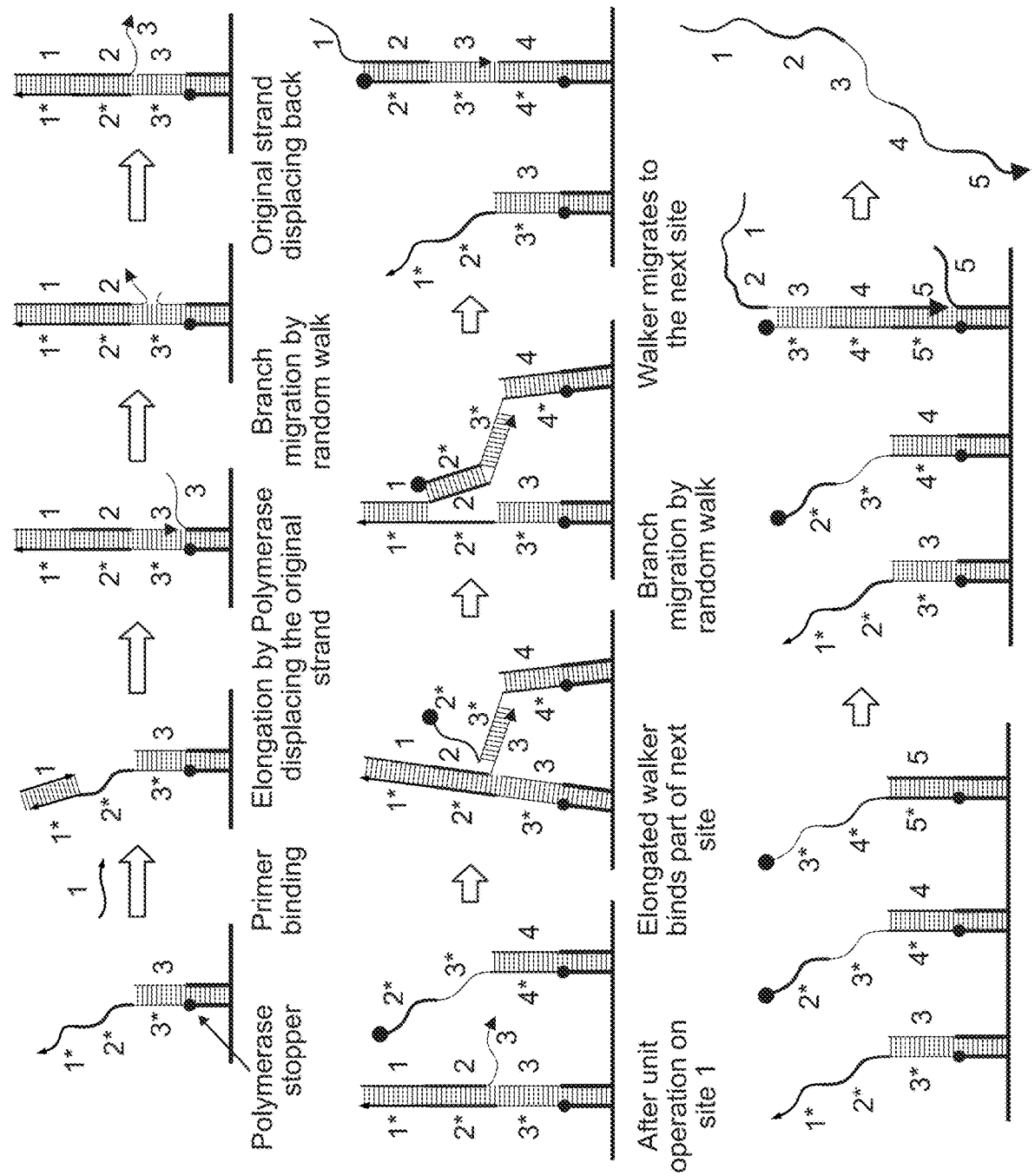
FIG. 6 shows a basic operation mechanism of an example of a molecular motor molecule (referred to as a "molecular walker"). The top row depicts the unit operations on a single site. The middle row depicts one step of walking between two neighboring sites. The bottom row depicts the initial and final states of three-site "track," where each site is a DNA-labeled amino acid in a protein chain of interest. The generated records can be released by multiple mechanisms. Circular arrowheads at the end of some strand species indicate modifications for protection against elongation by polymerases (e.g., inverted dT).

In some embodiments, the molecular instruments used to record and report protein sequence information are referred to as molecular motor molecules, which report chains of proximity information. FIGS. 5 and 6 show example of molecular motor systems for recording and reporting protein sequence information. A "molecular crawler" (FIG. 5) is a snake-like molecular species that roams around a track (e.g., a protein chain that includes DNA-labeled amino acids attached to barcoded catalytic molecules), spanning across the whole trajectory as it grows from the first track site (e.g., a DNA-labeled amino acid) to the final track site (see, e.g., FIG. 5). As the crawler moves between DNA-labeled amino acids, it copies the barcode from the barcoded catalytic molecule to which an amino acid is attached and "records" the sequence information in its growing body (elongating nucleic acid). A "molecular walker" moves between DNA-labeled amino acids, leaving the previous amino acid after each step (see, e.g., FIG. 6). While traveling along a protein chain, the walker grows its body, copying and retaining the information from the barcoded catalytic molecules.

The mechanisms of the unit operation on a single site (amino acid) are shown in the top rows of FIGS. 5 and 6. In both molecular motor systems, the reaction is initiated by binding of a primer (input signal; 'a' in FIG. 5 and '1' in FIG. 6) onto their complementary primer-binding domain (e.g., toehold domain) of the site. The next step is elongation of the primers by a polymerase along the template until the polymerase hits the "polymerase stopper" points (a molecule that terminates polymerization). DNA base monomers (dNTPs) are supplied in the system for the polymerase to add to the newly synthesized part. The stopping points can be encoded by one of the following two ways, for example. A non-nucleotide chemical spacer (e.g., triethylene glycol spacer) may be added as a stopper, or a subset of bases may be used in a system and the excluded base used as the stopper. Other molecules that terminate polymerization are described elsewhere herein. For example, if a three-letter code with A, T, and C in the template is used, their complement base monomers, A, T, and G, are supplied in the system, and G's are embedded at the end of the template. The polymerase cannot extend the new strand because the system does not have the complement base monomer, C. When the polymerase finishes the synthesis of the new domain and reaches the stopper point, it leaves (dissociates from) the template. Then, since the newly synthesized domain shares the same sequence as the template, it can undergo a random walk branch migration process. If the original template displaces the newly synthesized domain, a new primer for the next reaction is exposed.

After the unit operation, in both molecular motor systems, the first site has a newly synthesized domain that can now act as a primer for the next site. Since the molecular motor molecule (e.g., molecular crawler or molecular walker) is still anchored on the first site—the lengths of the relevant parts in the molecule will be designed to satisfy this condition—the new primer only acts locally on the sites in proximity. The movement mechanisms to the next sites are different between the two systems. In the molecular crawler system, the new primer binds the primer-binding domain (e.g., toehold domain) of the next site through complementarity, and the unit operation is repeated. The outcome is a molecular crawler with an extended body along the second site (middle row of FIG. 5). Note that the primer-binding domains (e.g., domain b* of the second site) should be protected against primer extension, to prevent spontaneous release of the crawler in the middle of the track; such protection is achieved by incorporating non-extendable bases, such as inverted-dT at the 3'-end of the strand, for example.

Figure 8A:
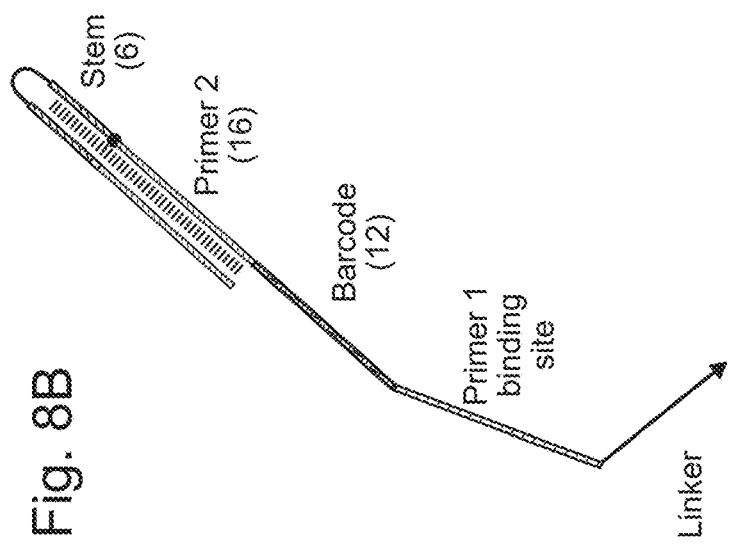
FIGS. 8A-8D show variations of the crawler probe design and their reach distances. The designs may comprise a primer 1 binding site, a barcode (12), a primer 2 (16), a stem (6), and a linker.
Figure 8B:
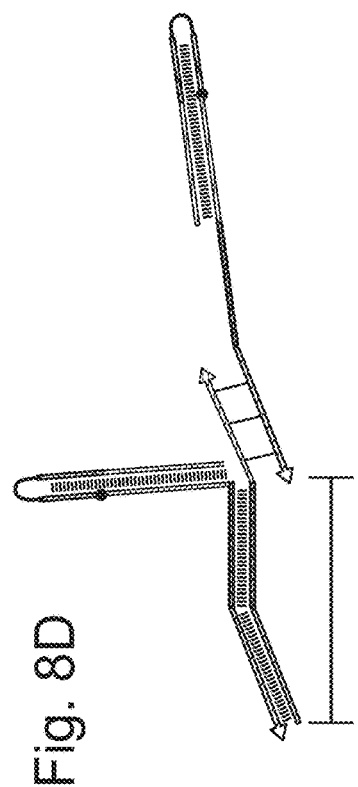
Figure 8C:
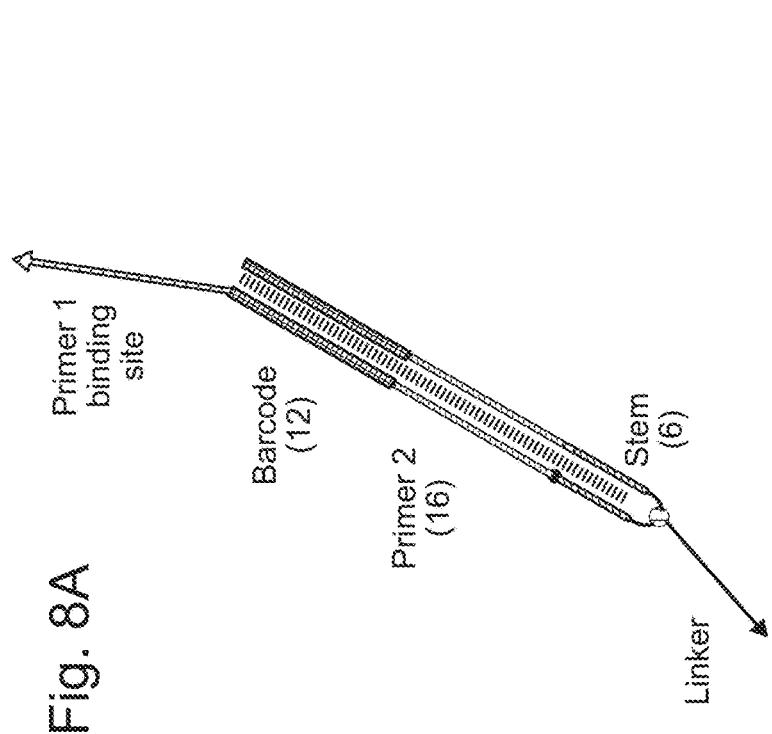
Figure 8D:
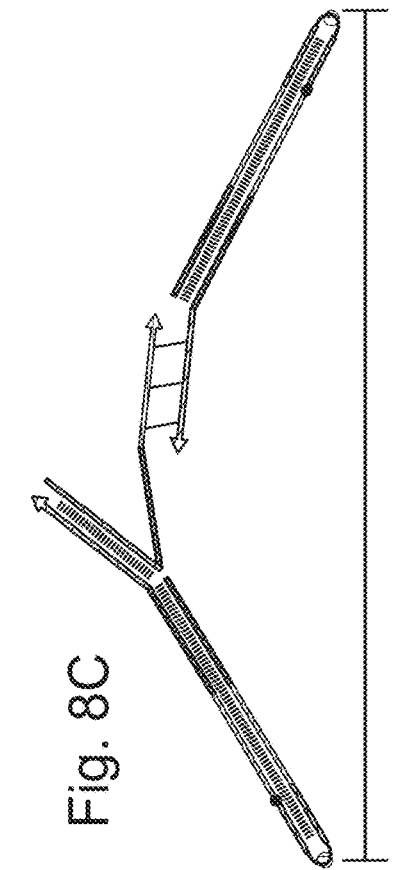
Figure 9:
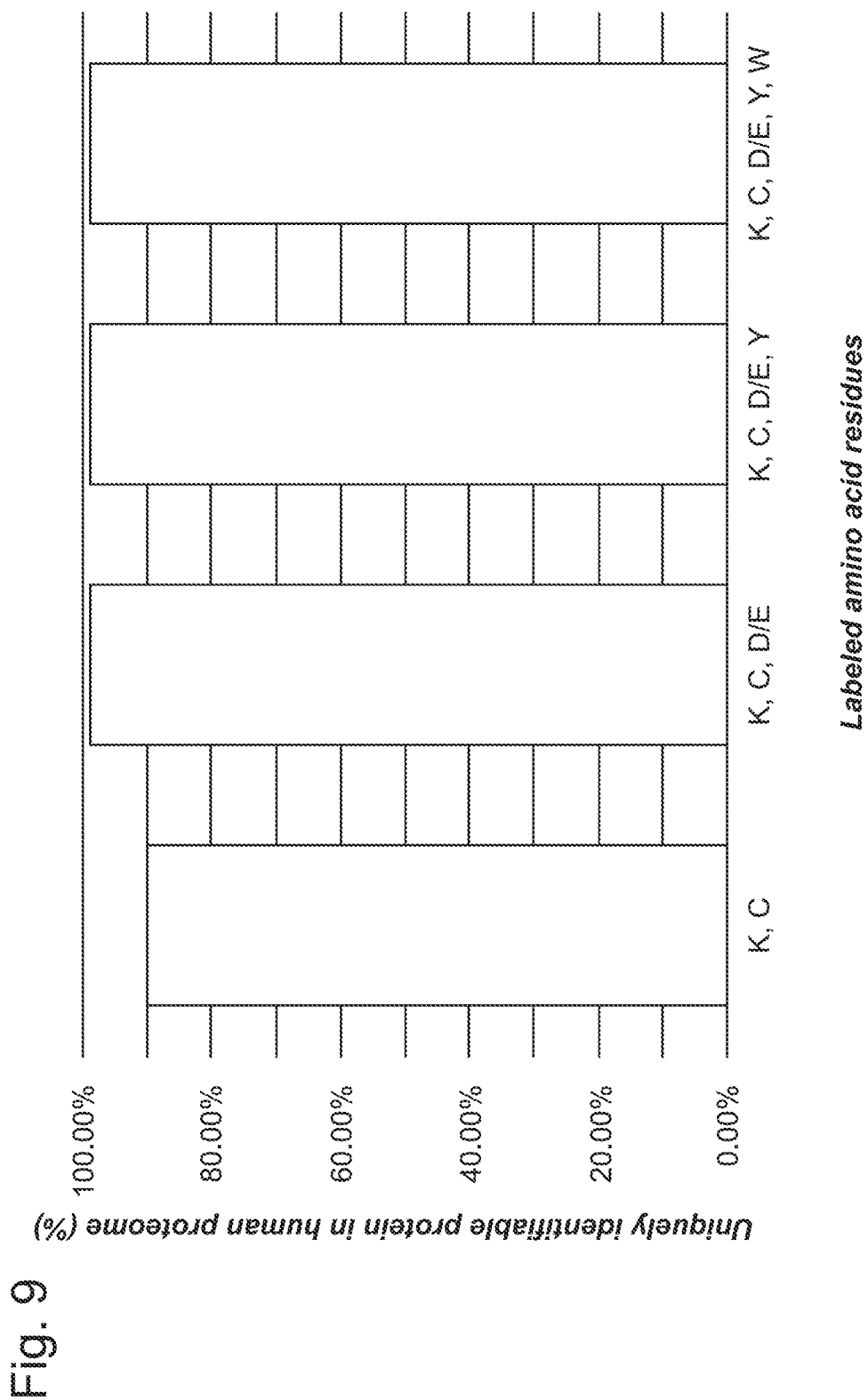
FIG. 9 shows a bar graph summarizing uniquely identifiable protein fractions by sequence information of different subsets of amino acid residues.

The molecular crawler probe, i.e., barcoded catalytic molecule bound to a DNA-labeled amino acid, may have different configurations, allowing for different reach distances. A "reach distance" is the distance between two adjacent probes (see, e.g., FIGS. 8C-8D). In one embodiment, an "upright" molecular probe, illustrated in FIGS. 8A, 8C, is used. The upright molecular crawler probe features a primer binding site at the farthest end of the probe ("primer 1 binding site"). Because the primer binding site is located at the farthest end of the probe, the reach distance can be much greater (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, or 55 nm). In another configuration, an "inverted" molecular crawler probe, depicted in FIGS. 8B and 8D, is used. The inverted molecular crawler probe comprises a primer binding site ("primer 1 binding site") between the linker and the barcode domains, leading to shorter reach distances between two adjacent probes with the same design (e.g., 1, 2, 3, 4, 5, 6, 7, 8, 9, 10, 11, 12, 13, 14, 15, 16, 17, 18, 19, or 20 nm). Further, the inverted molecular crawler probe comprises a linker which may be part of the probe DNA strand, as opposed to coupled to the probe at the bottom of the stem domain (e.g., by click chemistry). In some embodiments, the system uses only upright or only inverted molecular crawler probes. In other embodiments, the two molecular crawler probe designs are both used in a single system.

In some embodiments, a molecular crawler probe comprises a single-stranded nucleic acid containing, in the following 5' to 3' direction, a first domain, a second domain, a third domain, an unpaired loop domain, a fourth domain, a fifth domain, a sixth domain, and a seventh unpaired domain, wherein (a) the first and sixth domains are complementary to each other and contain a barcode sequence specific for a single amino acid, (b) the second and fifth domains are complementary to each other and contain a primer sequence that is designed, when copied to a growing strand (motor), to bind the unpaired seventh domain (primer binding site) of an adjacent probe, (c) the third and fourth domains are complementary to each other, (d) the unpaired loop domain is linked to a linker molecule (e.g., a single-stranded nucleic acid), and (e) a stopper molecule is located between the fourth and fifth domains. See, e.g., FIG. 8A. In some embodiments, provided herein is a composition comprising (a) a substrate to which a protein chain comprising amino acids labeled with barcoded DNA strands is attached and (b) at least 1 or at least 2 (e.g., at least 3, 4, 5, 6, 7, 8, 9 or 10) of the foregoing molecular crawler probes. In some embodiments, the linker molecule comprises a nucleotide sequence complementary to a nucleotide sequence of a barcoded DNA strand of the protein chain. In some embodiments, the composition further comprises at least one nucleic acid primer strand containing a sequence complementary to the seventh unpaired domain. In some embodiments, the first and/or sixth domain has a length of 10-30 nucleotides. In some embodiments, the second and/or fifth domain has a length of 10-20 nucleotides. In some embodiments, the third and/or fourth domain has a length of 5-30 nucleotides.

In some embodiments, a molecular crawler probe comprises a single-stranded nucleic acid containing, in the following 5' to 3' direction, a first domain, a second domain, an unpaired loop domain, a third domain, a fourth domain, an unpaired fifth domain, and an unpaired sixth domain, wherein (a) the first and fourth domains are complementary to each other and contain a primer sequence that is designed, when copied to a growing motor, to bind the primer binding site (unpaired sixth domain) of an adjacent probe, (b) the second and third domains are complementary to each other, (c) the fifth domain contains a barcode sequence containing two sub-domains, first being specific for a single amino acid and second being specific for the particular probe molecule, (d) a stopper molecule is located between the third and fourth domains, and (e) the unpaired sixth domain is linked to a linker molecule (e.g., a single-stranded nucleic acid). See, e.g., FIG. 8B. In some embodiments, provided herein is a composition comprising (a) a substrate to which a protein chain comprising amino acids labeled with barcoded DNA strands is attached and (b) at least 1 or at least 2 (e.g., at least 3, 4, 5, 6, 7, 8, 9 or 10) of the foregoing molecular crawler probes. In some embodiments, the linker molecule comprises a nucleotide sequence complementary to a nucleotide sequence of a barcoded DNA strand of the protein chain. In some embodiments, the composition further comprises at least one nucleic acid primer strand containing a sequence complementary to the sixth unpaired domain. In some embodiments, the first and/or fourth domain has a length of 10-20 nucleotides. In some embodiments, the second and/or third domain has a length of 5-30 nucleotides. In some embodiments, the fifth domain has a length of 10-30 nucleotides.

In the molecular walker system, the walker molecule undergoes a competitive branch migration process between the current and the next sites (middle row of FIG. 6). If the second site displaces the corresponding part of the first site, the walker can be transported to the second site; the lengths of the primers should be designed such that the binding of one primer to its complement (e.g., between domains 1 and 1*) is weak enough to release the walker from the previous site, while the binding of two consecutive primers to their complement (e.g., between domains 1-2 and 2*-1*) is strong enough to hold the walker on the next site. However, since the walker still contains a domain that is complementary to the primer-binding domain of the previous site, the motion of a walker is reversible (can walk back). This can be a feature in cases where revisits of multiple sites are necessary, e.g., in maze solving. Note that the track sites recover their original form after a walker leaves the sites, thus becoming reusable.

After repeating the steps along three adjacent sites (bottom rows of FIGS. 5 and 6), the snake-like molecular crawler now spans across the whole track (e.g., protein chain), while the walker has traversed to the final site (e.g., barcoded catalytic molecule bound to a DNA-labeled amino acid). The release of the crawlers, for retrieval of the record and history, can be implemented by multiple methods. In one example, at the end of recording reaction, a "reverse primer" can be added to synthesize a complement copy of the crawler, displacing the crawler off of the protein chain. For example, a primer with the domain "d*" in the case of the snake-like crawler, and a primer with the domain "5*" in the case of walker, can initiate such a reverse copy process. As another example, a more simple mechanism, based on heat-mediated dehybridization of motors can be used. While system-wide heat could also denature the barcoded catalytic molecules or some components, selective detection of target signals is possible, when combined, for example, with PCR amplification with specific primers.

Molecular motor systems, in some embodiments, use molecular instruments for parallel "bottom-up" inspection of large populations of molecular-scale targets. Molecular records may be repeatedly created along a substrate comprising individual protein chains, each amino acid labeled with a barcoded DNA anchor sequence, without disturbing or destroying the amino acids themselves, and later read by high-throughput sequencing for computational reconstruction of the protein chain. With molecular motor systems (e.g., molecular crawlers and molecular walkers), amino acids of a protein chain are linked to barcoded catalytic nucleic acid (e.g., DNA) molecules that drive movement of the molecular crawlers and walkers. As shown in FIGS. 5 and 6, an amino acid may be linked to a barcoded catalytic molecule having (i) an unpaired 3' toehold domain and (ii) a paired domain (containing the barcode) located 5' from the toehold domain that is formed by base pairing between nucleotides of a displacement strand and nucleotides of a template strand containing the toehold domain.

With reference to FIG. 5, the unpaired 3' toehold domain (similar to the toehold domain of the APR system discussed above) is denoted by 'a*'. The nucleic acid strand containing the unpaired toehold domain is referred to as the "template strand." This is the strand to which the primer anneals to initiate polymerization. The opposing strand, to which the template strand is bound (paired, hybridized), is referred to as the "displacement strand." Subdomains '1' and 'b' of the displacement strand pair respectively with subdomains '1*' and 'b*' of the template strand to form the paired domain located 5' from the toehold domain. During polymerization initiated by binding of the primer to the toehold domain of the template strand, the displacement strand is initially displaced by the elongation product. Subsequently, however, the displacement strand displaces the elongation product and binds again to template strand (a process referred to as branch migration) (top row). The elongation product, now containing information ('1') from the initial amino acid of a protein chain is then free to function as a primer and bind to the toehold domain of another molecular linked to an amino acid, starting another cycle of the elongation/branch migration process (middle row). With each cycle, a record of information from each DNA-labeled amino acid is added to a growing nucleic acid polymer strand, referred to as the molecular crawler (bottom row, '1+2+3').

With reference to FIG. 6, the unpaired 3' toehold domain is denoted by '1*'+'2*'. The nucleic acid strand containing the unpaired toehold domain is the template to which primer '1' anneals to initiate polymerization. The opposing strand, to which the template strand is bound (paired, hybridized), is the displacement strand. Subdomain '3' of the displacement strand pairs with subdomain '3*' of the template strand to form the paired domain located 5' from the toehold domain. During polymerization initiated by binding of the primer to the toehold domain of the template strand, the displacement strand is initially displaced by the elongation product. Subsequently, however, the displacement strand displaces the elongation product and binds again to template strand (top row). The elongation product, now containing information from the initial molecular site is then free to function as a primer and bind to the toehold domain (in this case, to subdomain '3*' of the toehold domain) of another molecular site, starting another cycle of the elongation/branch migration process (middle row). With each cycle, a record of information from each molecular motor (each interaction between molecular motors) is added to a growing nucleic acid polymer strand, referred to as the molecular walker (bottom row, '1+2+3+4+5').

An amino acid of a protein chain, in a molecular motor system, generally is linked to a "barcoded catalytic molecule" (similar to the barcoded catalytic molecules described above) that includes an unpaired (single-stranded) 3' toehold domain and a barcoded paired (double-stranded) stem domain located 5' from the 3' toehold domain. In some embodiments, the paired domain is directly adjacent to the toehold domain. The barcode identifies both the type of amino acid and the specific catalytic molecule. For example, a barcode of a catalytic molecule may include a sequence that is unique to a particular type of amino acid (e.g., unique to lysine only) and may also include another sequence, randomly assigned, that is unique to the catalytic molecule. This permits a growing nucleic acid body to record the identity and relative position of an amino acid in a protein chain.

The length of a barcoded catalytic molecule may vary. In some embodiments, a barcoded catalytic molecule has a length of 25-300 nucleotides. For example, a barcoded catalytic molecule may have a length of 25-250, 25-200, 25-150, 25-100, 25-50, 50-300, 50-250, 50-200, 50-150 or 50-100 nucleotides. In some embodiments, a barcoded catalytic molecule has a length of 30-50, 40-60, 50-70, 60-80, 70-90, 80-100, 100-125, 100-150 or 100-200 nucleotides. In some embodiments, a barcoded catalytic molecule has a length of 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides. A barcoded catalytic molecule, in some embodiments, is longer than 300 nucleotides, or shorter than 25 nucleotides.

A "toehold domain," discussed above, refers to an unpaired sequence of nucleotides located at the 3' end of a barcoded catalytic molecule and is complementary to (and binds to) a nucleotide sequence of a primer (or primer domain of a primer). A toehold domain is typically a primer-binding domain. The length of a toehold domain may vary. In some embodiments, a toehold domain has a length of 5-40 nucleotides. For example, a toehold domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a toehold domain has a length of 5, 10, 15, 20, 25, 30, 35 or 40 nucleotides. In some embodiments, a toehold domain has a length of 10, 11, 12, 13, 14, 15, 16, 17, 18, 19, 20, 21, 22, 23, 24 or 25 nucleotides. A toehold domain, in some embodiments, is longer than 40 nucleotides, or shorter than 5 nucleotides.

In some embodiments, a toehold domain has subdomains (e.g., two subdomains), as depicted, for example, in FIG. 6. In such embodiments, a primer typically binds to the most 3' subdomain ('1*'). That is, the primer used in the molecular motor reaction does not necessarily span the entire length of the toehold domain—it may bind to only a subdomain (a portion of) the toehold domain.

A "paired domain" of a barcoded catalytic molecule refers to a paired sequence of nucleotides (e.g., Watson-Crick nucleobase pairing) located adjacent to (and 5' from) the unpaired toehold domain of a track site. The paired domain of a barcoded catalytic molecule is formed by base pairing between domain(s) of the template strand and domain(s) of the displacement strand. The length of a paired domain may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

In some embodiments, extension of a primer (bound to a primer-binding site) by a strand displacement polymerase is terminated by the presence of a molecule or modification in the track site that terminates polymerization. Thus, in some embodiments, track sites molecular motors of the present disclosure comprise a molecule or modification that terminates polymerization. A molecule or modification that terminates polymerization ("stopper") is typically located in a paired domain on the template strand of a track site such that polymerization terminates extension of the primer through the paired domain. In some embodiments, the molecule that terminates polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the paired domain, at the stopper position, the polymerase will be halted, as it does not have a complementary nucleotide in solution to add at that position.

In some embodiments, the efficiency of performance of a "stopper" modification is improved by lowering dNTP concentrations (e.g., from 200 µM) in a reaction to 100 µM, 10 µM, 1 µM, or less.

Inclusion of a molecule or modification that terminates polymerization often creates a "bulge" in a paired domain of catalytic molecule (e.g., a stem domain for hairpin structures), because the molecule or modification is not paired. Thus, in some embodiments, track sites for molecular motors include, opposite the molecule or modification, a single nucleotide (e.g., thymine), at least two of same nucleotide (e.g., a thymine dimer (TT) or trimer (TTT)), or a non-natural modification.

Molecular motor systems, in addition to barcoded catalytic molecule, include primers, referred to as input primers or output primers, which get extended to become molecular crawlers and/or molecular walkers. Primers are described elsewhere herein.

A complete "step" of a molecular motor reaction is depicted in FIG. 5. An input primer ('a') binds to a toehold domain ('a*') of a barcoded catalytic molecule (linked to an amino acid) to start the reaction. Upon binding to the barcoded catalytic molecule in reaction solution containing polymerase (e.g., strand displacing polymerase) and dNTPs, the initial primer is extended through the paired domain, displacing the displacement strand (subdomains '1+b') of the paired domain. The displaced strand then competes with the extended primer for binding (reannealing) with its complementary binding domain on the template strand, thereby displacing the extended output primer. This completes a step of the reaction. The displaced output primer "1+b" may then go on to function as an input primer in the next step of the reaction.

In some embodiments, a primer or primer domain (the nucleotide sequence that binds to the toehold domain of a barcoded catalytic molecule) has a length of 10-50 nucleotides. For example, a primer or primer domain may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, a primer or primer domain has a length of 10, 15, 20, 25, 30, 35, 40, 45 or 50 nucleotides. In some embodiments, a primer or primer domain has a length of 15, 16, 17, 18, 19, 20, 21, 22, 23, 24 or 25 nucleotides. A primer or primer domain, in some embodiments, is longer than 50 nucleotides, or shorter than 10 nucleotides. It should be understood that the full length of a primer depends, at least in part, on the number and length of appended (polymerized) sequences, which depends on the number and length of barcoded catalytic molecule present in a reaction.

A primer, as provided herein, may be linked to (labeled with) a detectable molecule (e.g., a molecule that emits a detectable signal, such as a fluorescent or chemiluminescent signal). In some embodiments, the label is a fluorophore. A primer linked to a fluorophore or other fluorescent/chemiluminescent molecule is referred to simply as a "fluorescent primer." Examples of fluorophores that may be used herein include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660, Cy5.5, TruRed, Alexa fluor 680, Cy7 and Cy7.5. Other fluorophores and molecules that emit a detectable signal are encompassed by the present disclosure.

In some embodiments, a detectable molecule is linked to the barcoded catalytic molecule rather than the primer.

Molecular motor systems require the use of a polymerase. In some embodiments, the polymerase is a DNA polymerase (DNAP), such as a DNA polymerase having DNA strand displacement activity. "Strand displacement" describes the ability to displace downstream DNA encountered during synthesis. Examples of polymerases having DNA strand displacement activity that may be used as provided herein include, without limitation, phi29 DNA polymerase (e.g., NEB # M0269), Bst DNA polymerase, large fragment (e.g., NEB # M0275), or Bsu DNA polymerase, large fragment (e.g., NEB # M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: 1× reaction buffer (e.g., 50 mM Tris-HCl, 10 mM $MgCl_2$, 10 mM $(NH_4)_2SO_4$, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1× reaction buffer (e.g., 20 mM Tris-HCl, 10 mM $(NH_4)_2SO_4$, 10 mM KCl, 2 mM $MgSO_4$, 0.1% TRITON® X-100), pH 8.8, incubated at 65° C.

In some embodiments, the polymerase is Bsu DNA polymerase. In such embodiments, the reaction conditions may be as follows: 1× reaction buffer (e.g., 50 mM NaCl, 10 mM Tris-HCl, 10 mM $MgCl_2$, 1 mM DTT), pH 7.9, incubated at 37° C.

The concentration of primer, molecular tracks and dNTPs in a reaction system may be varied depending, for example, on the particular application and kinetics required for that particular application.

The concentration of primer in a reaction may be, for example, 10 nM to 1000 nM. In some embodiments, the primer concentration in a reaction is 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 nM. In some embodiments, the primer concentration in a reaction is 100-200, 100-300, 100-400, 100-500, 100-600, 100-70, 100-800, 100-900 or 100-1000 nM. In some embodiments, the primer concentration in a reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the primer concentration in a reaction is 100, 200, 300, 400, 500, 600, 700, 800, 900 or 1000 nM. The concentration of primer in a reaction may be less than 10 nM or greater than 1000 nM.

The concentration of barcoded catalytic molecules in a reaction may be, for example, 5 nM to 1000 nM. In some embodiments, barcoded catalytic molecule concentration in a reaction is 5-10, 5-20, 5-30, 5-40, 5-50, 5-60, 5-70, 5-80, 5-90, 5-100, 5-125, 5-150, 5-200, 10-50, 10-75, 10-100, 10-150, 10-200, 25-75, 25-100, 25-125 or 25-200 nM. In some embodiments, the barcoded catalytic molecule concentration in a reaction is 10-200, 10-300, 10-400, 10-500, 10-600, 10-70, 10-800, 10-900 or 10-100 nM. In some embodiments, the barcoded catalytic molecule concentration in a reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the barcoded catalytic molecule concentration in a reaction is 10, 20, 30, 40, 50, 60, 70, 80, 90 or 100 nM. The concentration of barcoded catalytic molecule in a reaction may be less than 5 nM or greater than 1000 nM.

The ratio of primer to barcoded catalytic molecule in reaction may be 2:1 to 100:1. In some embodiments, the ratio of primer to molecular motor is 2:1, 3:1, 4:1, 5:1, 6:1, :1, 8:1, 9:1, 10:1, 11:1, 12:1, 13:1, 14:1, 15:1, 16:1, 17:1, 18:1, 19:1 or 20:1. In some embodiments, the ratio of primer to barcoded catalytic molecule is 30:1, 40:1, 50:1, 60:1, 70:1, 80:1 or 90:1.

The number of different barcoded catalytic molecules in a reaction is non-limiting. A reaction may comprise $1\text{-}10^{10}$ different barcoded catalytic molecules (each with a specific toehold domain sequence, for example). In some embodiments, a reaction comprises 1-10, $1\text{-}10^2$, $1\text{-}10^3$, $1\text{-}10^4$, $1\text{-}10^5$, $1\text{-}10^6$, $1\text{-}10^7$, $1\text{-}10^8$, $1\text{-}10^9$, $1\text{-}10^{10}$, or more, different barcoded catalytic molecules. In some embodiments, a reaction comprises 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 10-15, 10-20, 10-25, 10-30, 10-35, 10-40, 10-45, 10-50, 10-55, 10-60, 10-65, 10-70, 10-75, 10-80, 10-85, 10-90, 10-95 or 10-100 different barcoded catalytic molecules. In some embodiments, a reaction comprises 1, 2, 3, 4, 5, 6, 7, 8, 9, 10, 11, 12, 13, 14, 15, 16, 17, 28, 19, 20, 21, 22, 23, 24 or 25 different barcoded catalytic molecules. Barcoded catalytic molecules are different from each other if their toehold domains differ from each other, for example.

The kinetics of a reaction may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, the temperature at which a reaction is performed may vary from, for example, 4° C. to 65° C. (e.g., 4° C., 25° C., 37° C., 42° C. or 65° C.). In some embodiments, the temperature at which a reaction is performed is 4-25° C., 4-30° C., 4-35° C., 4-40° C., 4-45° C., 4-50° C., 4-55° C., 4-60° C., 10-25° C., 10-30° C., 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a reaction is performed at room temperature, while in other embodiments, a reaction is performed at 37° C.

A reaction may be performed (incubated) for 30 minutes (min) to 24 hours (hr). In some embodiments, a reaction is carried out for 10 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr.

The concentration of dNTPs in a reaction may be, for example, 2-1000 µM. In some embodiments, the dNTP concentration in a reaction is 2-10 µM, 2-15 µM, 2-20 µM, 2-25 µM, 2-30 µM, 2-35 µM, 2-40 µM, 2-45 µM, 2-50 µM, 2-55 µM, 2-60 µM, 2-65 µM, 2-70 µM, 2-75 µM, 2-80 µM, 2-85 µM, 2-90 µM, 2-95 µM, 2-100 µM, 2-110 µM, 2-120 µM, 2-130 µM, 2-140 µM, 2-150 µM, 2-160 µM, 2-170 µM, 2-180 µM, 2-190 µM, 2-200 µM, 2-250 µM, 2-300 µM, 2-350 µM, 2-400 µM, 2-450 µM, 2-500 µM, 2-600 µM, 2-700 µM, 2-800 µM, 2-900 µM or 2-1000 µM. For example, the dNTP concentration in a reaction may be 2 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM or 200 µM. In some embodiments, the dNTP concentration in a reaction is 10-20 µM, 10-30 µM, 10-40 µM, 10-50 µM, 10-60 µM, 10-70 µM, 10-80 µM, 10-90 µM or 10-100 µM.

In some embodiments, dNTP variants are used. For example, molecular motor systems may use hot start/clean amp dNTPs, phosphorothioate dNTPs, or fluorescent dNTPs. Other dNTP variants may be used.

EXAMPLES

Example 1

Provided herein is an example of a protein fingerprinting method based on identification of each individual protein molecules at the single-molecule level, enabled by the action of swarms of DNA probes (molecular instruments) that enable inspection and reconstruction of protein chains. This system can be used to convert protein sequence information into nucleic acid sequence information, which can then be recorded and reported by the DNA probes.

Protein fingerprinting, in this example, is performed as follows (see, e.g., FIG. 1). (1) Protein molecules are attached to a surface and denatured and stretched. Protein molecules are fixed on a surface by N-terminal or C-terminal specific chemical coupling methods. The surface-bound protein molecules are denatured by common denaturants such as urea or sodium dodecyl sulfate, and can be stretched by applying external forces, e.g., by attaching a magnetic bead at the end far from the surface and applying magnetic field, by using an electrically charged particle and electric field in a similar fashion, or by applying centrifugal forces. (2) A subset of amino acid residues are barcoded with DNA strands containing a unique identifier, in an amino acid specific manner. Chemical coupling between DNA and amino acid residues is achieved through amino-acid-specific chemical modification methods; for example, lysine residues are modified with NHS-ester chemistry and cysteine residues selectively interact with the maleimide group. In addition to encoding the amino acid species information, each copy of DNA probe also has a unique molecular identifier (UMI, e.g. by using randomized sequences; FIG. 2, inset) for each specific site. (3) DNA probes record the proximity information via either of the two mechanisms: autocyclic proximity recording (APR) or molecular crawlers. Typical reactions happen in the following fashion: sample is mixed with a solution containing DNA primers, deoxynucleotide (dNTP), and strand-displacing DNA polymerase (e.g., Bst or Bsm) and incubated for ~2 hours either at room temperature or 37° C. During the reaction, each target site is recorded multiple times with different neighboring probe partners at any distance within the reach of the probe (from sub-6 nm to ~30 nm), generating partially overlapping records (e.g., proximity records A-B, B—C and A-C can be made for sites A, B, and C if they are all within the reach distance). (4) Records are released and collected; records are released into solution by in situ synthesis of a complementary strand, or by heat-mediated dehybridization. Production of records is characterized by gel electrophoresis. Gel analysis allows the confirmation of the formation of records with expected lengths as well as quantitative characterizations of record length distribution. (5) Retrieved records are processed for next-generation sequencing (NGS); records are amplified by e.g., polymerase chain reaction (PCR), and linked to adapter strands to be compatible with common NGS platforms such as Illumina MiSeq. Then the records are sequenced at the single-molecule level by NGS. Sequencing reads are then parsed to allow identification of unique barcode sequences and pairwise relationships. (6) The redundant and partially overlapping records information is used to computationally reconstruct the arrangement of the labeled amino acids. The labeled amino acids represent a subset of the full amino acid sequence of the target protein. (7) This sub-sequence information is then compared to human proteome database (e.g., UniProtKB/Swiss-Prot complete *H. sapiens* proteome, comprising 20170 identified protein sequences), and the identity of the protein can thus be revealed.

Example 2

The molecular instruments copy and record the information from amino acids through DNA strand labels. In addition to encoding the amino acid species information (e.g., lysine, K, or cysteine, C), each copy of the DNA probes also contain a unique molecular identifier (UMI, e.g. by using randomized sequences). FIG. 2 describes how to encode both kinds of information at each probe for the APR scheme, but the same principle is also applied to the molecular crawler scheme. A specific amino acid (e.g., cysteine, C) is labeled with a specific anchor DNA sequence ("Anchor for C"). Probes binding to these anchors contain barcode sequences that indicate "C". In addition, each probe molecule contains a unique barcode sequence created by randomized sequences during synthesis of the probes (denoted by "i", "j", etc., in the figure). Thus, all probes binding to the cysteine residues will contain the same barcode sequence for C; however, each of those probes will have different identifier sequence unique to each probe. This allows identification of each molecular label from the records, hence enabling the mapping of the set of proximity information to specific locations of the protein chains.

Example 3

A series of tests were performed for one of the molecular motor molecules, referred to as a "crawler." The tests confirmed the basic operations, as shown in FIG. 7. A three-point track was designed along a triangular alignment on a DNA nanostructure platform. FIG. 7, left top image, depicts a schematic of the design, and FIG. 7, left bottom image, shows the molecular detail of a crawler after crawling over the three target sites. Once completing the crawling process, the crawlers become the full record of length 118 nt. When amplified by PCR and run on a denaturing gel, the final records appear at the expected length range (FIG. 7, middle image). The crawlers were also visualized using an atomic force microscope (AFM). FIG. 7, right image (before recording) shows the target probes before the primers initiating the crawling reaction were added, where the probes appear as dots. After the recording reaction of about 1 hour, crawlers now connect the three track sites together as shown in FIG. 7, left bottom image, and thus appear accordingly in the AFM images (FIG. 7, right image (after recording). These test results demonstrate the basic operation of the crawler system for each step: (1) primer binding, (2) primer extension by a polymerase, (3) strand displacement by the template, (4) interaction with a neighboring site, (5) additional extension by a polymerase, and (6) autonomous release of the records.

Reaction Conditions:
Recorded with Bst for 1 hr at RT
[recording primer]=100 nM
[reverse primer]=10 nM
[dNTP]=100 µM
Probes/origami fixed on mica
No reverse primer for AFM tests
PCR amplification 20 cycles
8% denaturing PAGE Example 4

Figure 10:
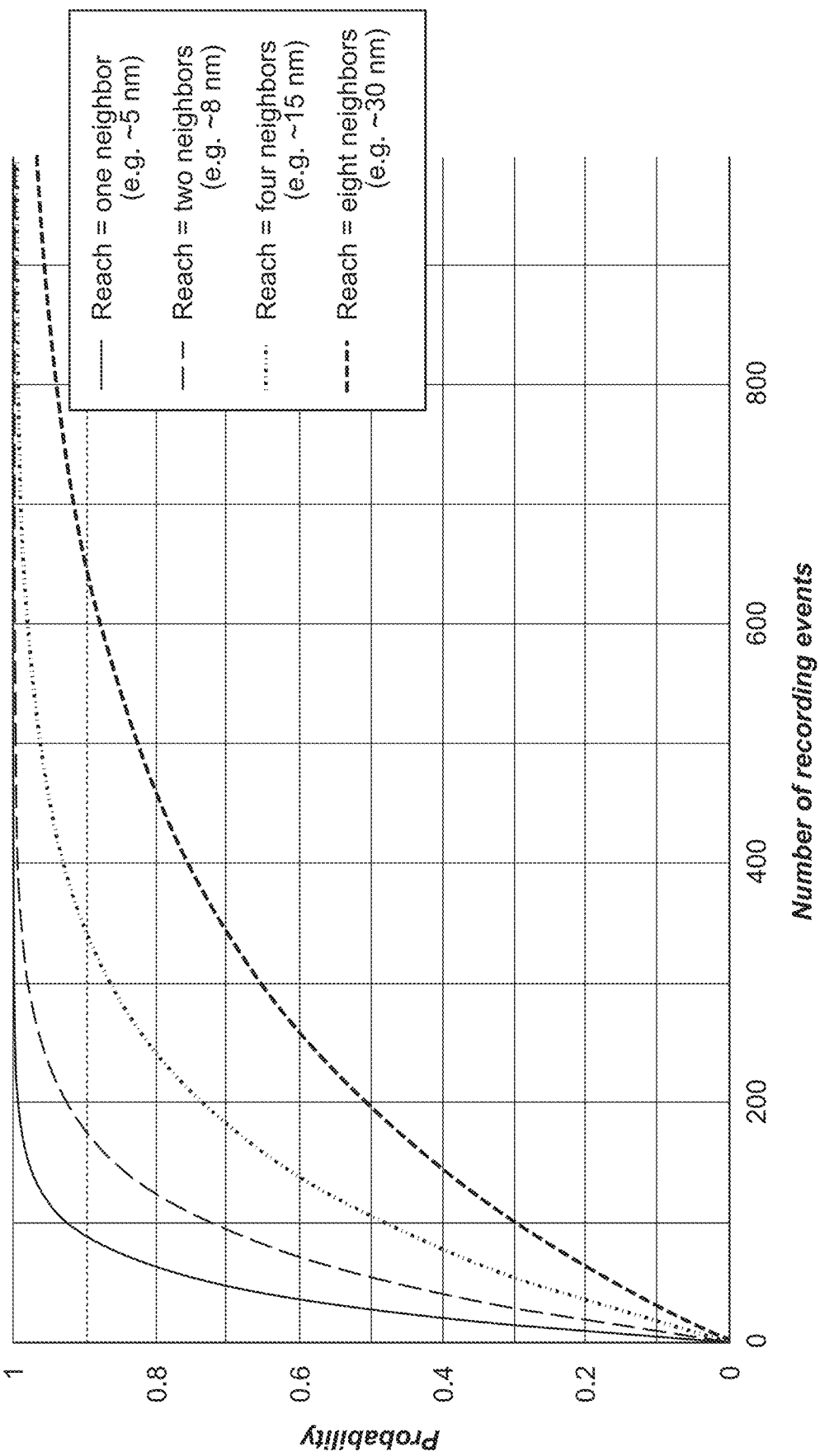
FIG. 10 shows a plot of the probability that one particular probe pair is visited at least once in varying numbers of recording events, for different probe reach distances. The probability estimation is based on binomial distribution and indicates that to cover ~90% pairwise relationships, ~80 records are needed if the probe reach is within about one neighbor (average ~3.5 nm apart), and ~650 records are needed if the reach is within about eight neighbors (e.g., ~30 nm).

An analysis on human proteome (UniProtKB/Swiss-Prot complete *H. sapiens* proteome, comprising 20170 protein sequences, not considering alternatively spliced isoforms) shows that knowing the sequence information allows unique identification of ~90% proteins with only K and C labeling, and higher coverage with further labeling (D/E, Y, or W) (FIG. 10).

Example 5

A throughput estimation based on binomial distribution indicates that to cover ~90% of pairwise relationships, ~80 records are needed if the probe reach is within about one neighbor (average ~3.5 nm apart), and ~650 records are needed if the reach is within about eight neighbors (e.g., ~30 nm). The throughput estimation was calculated based on an approximately 400 amino acid protein with a combined relative abundance of K and C amino acids of 10% (~40 sites per protein, ~3.5 nm apart on average). With these requirements for number of records, common NGS platforms (MiSeq: ~25×$10^6$, HiSeq: ~6×$10^9$ reads/run) would allow analysis of maximum ~$10^5$-$10^8$ proteins per run for shorter reach and ~$10^4$-$10^7$ proteins per run for longer reach (assuming no sampling bias).

Example 6

An example of protein fingerprinting and protein sequencing using the methods described herein is given. Protein molecules may be accompli the sample is mixed with a solution comprising DNA primers, deoxynucleotides (dNTPs), and strand-displacing polymerase (e.g., Bst or Bsm). The composition is then incubated for approximately 2 hours at around 37° C. During the incubation period, each target site is recorded multiple times with different neighboring probe partners at any distance within the reach of the probe ( All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    combining in reaction buffer comprising a polymerase having strand displacement activity
    (a) a substrate to which a protein chain comprising amino acids labeled with barcoded DNA strands is attached,
    (b) at least two barcoded catalytic molecules, wherein each barcoded catalytic molecule comprises (i) an unpaired 3' toehold domain, (ii) a paired stem domain formed by intramolecular nucleotide base pairing between a 3' subdomain and a 5' subdomain, wherein the paired stem domain comprises a first barcode sequence that identifies a type of amino acid and a second barcode sequence that identifies each barcoded catalytic molecule, (iii) a paired palindromic domain, and (iv) a loop domain linked to a DNA strand that is complementary to a barcoded DNA strand coupled to an amino acid of the protein chain, and
    (c) at least one primer, wherein the primer is complementary to and binds to the 3' toehold domain of the barcoded catalytic molecules of (b), thereby forming a reaction mixture; and
    incubating the reaction mixture under conditions that result in nucleic acid polymerization, strand displacement and annealing, for a time sufficient to produce a nucleic acid record.

2. The method of claim 1 further comprising
    attaching the protein to the substrate;
    denaturing the protein;
    stretching the protein to form a protein chain having one end attached to the substrate and the other end not attached to the substrate; and
    chemically coupling, to amino acids of the protein chain, barcoded DNA strands, wherein each barcoded DNA strand uniquely identifies a type of amino acid, thereby forming a DNA-labeled protein chain.

3. The method of claim 2, wherein the protein is attached to the surface using a N-terminal-specific chemical coupling method or a C-terminal-specific chemical coupling method.

4. The method of claim 2, wherein the protein is denatured using urea or sodium dodecyl sulfate.

5. The method of claim 2, wherein the protein is stretched by applying external forces to the protein.

6. The method of claim 5, wherein applying external forces includes attaching a magnetic bead to the end of the protein that is not attached to the substrate and applying a magnetic field to the magnetic bead.

7. The method of claim 5, wherein applying external forces includes attaching an electrically-charged particle to the end of the protein that is not attached to the substrate and applying an electric field to the electrically-charged particle.

8. The method of claim 2, wherein the barcoded DNA strands are modified with NHS-ester and are chemically coupled to amine-based amino acids of the protein.

9. The method of claim 1, wherein the substrate comprises glass.

10. The method of claim 1, wherein the polymerase is selected from Bst polymerases, phi29 polymerases, Deep Vent polymerases, Vent polymerases, Klenow fragment polymerases, and Taq polymerases.

11. The method of claim 1, wherein the barcoded DNA strands have a length of 10-100 nucleotides.

12. The method of claim 11, wherein the barcoded DNA strands have a length of 50 nucleotides.

13. The method of claim 1, wherein each domain of the barcoded catalytic molecules has a length of 5-20 nucleotides.

14. The method of claim 1, wherein each domain of the primer has a length of 5-20 nucleotides.

15. The method of claim 1, wherein the reaction mixture is incubated at a temperature of 20-40° C.

16. The method of claim 1, wherein the reaction mixture is incubated for 10 minutes to 3 hours.

17. The method of claim 1 further comprising collecting the nucleic acid records.

18. The method of claim 17 further comprising sequencing the nucleic acid records and reconstructing the amino acid sequences.

19. The method of claim 18 further comprising comparing the reconstructed amino acid sequences to a database of known protein sequences or to a genome.

20. The method of claim 19 further comprising identifying the protein based on a comparison between the reconstructed amino acid sequences from the nucleic acid records to a database or library of known protein sequences or the genome.

21. A method, comprising:
combining in reaction buffer comprising a polymerase having strand displacement activity
(a) a substrate to which a protein chain comprising amino acids labeled with barcoded DNA strands is attached,
(b) an initial barcoded catalytic molecule comprising (i) an unpaired 3' toehold domain, (ii) a paired domain located 5' from the toehold domain that is formed by nucleotide base pairing between a displacement strand and a template strand containing the toehold domain, wherein the paired stem domain comprises a first barcode sequence that identifies a type of amino acid and a second barcode sequence that identifies the initial barcoded catalytic molecule, and (iii) a loop domain linked to a DNA strand that is complementary to a barcoded DNA strand coupled to an amino acid of the protein chain,
(c) a second barcoded catalytic molecule comprising (i) an unpaired 3' toehold domain, (ii) a paired domain located 5' from the toehold domain that is formed by nucleotide base pairing between a displacement strand and a template strand containing the toehold domain, wherein the paired stem domain comprises a first barcode sequence that identifies a type of amino acid and a second barcode sequence that identifies the second barcoded catalytic molecule, and (iii) a loop domain linked to a DNA strand that is complementary to a barcoded DNA strand coupled to an amino acid of the protein chain,
wherein the unpaired 3' toehold domain of the second nucleic acid molecule is complementary to the displacement strand of the initial nucleic acid molecule, and
(d) a primer complementary to nucleotides located in the unpaired 3' toehold domain of the initial nucleic acid molecule, thereby forming a reaction mixture; and
incubating the reaction mixture under conditions that result in nucleic acid polymerization, strand displacement and annealing, for a time sufficient to produce a nucleic acid record.

22. A method, comprising:
combining in reaction buffer comprising a polymerase having strand displacement activity
(a) a substrate to which a protein chain comprising amino acids labeled with barcoded DNA strands is attached, wherein each of the barcoded DNA strands uniquely identifies a type of amino acid, and
(b) barcoded molecular instruments that bind to the DNA strands and produce nucleic acid records of the barcoded DNA strands; and
incubating the reaction mixture under conditions that result in nucleic acid polymerization, strand displacement and annealing, for a time sufficient to produce the nucleic acid records.

23. The method of claim 22 further comprising collecting the nucleic acid records.

24. The method of claim 23 further comprising sequencing the nucleic acid records and reconstructing the amino acid sequences.

25. The method of claim 24 further comprising comparing the reconstructed amino acid sequences to a database of known protein sequences or to a genome.

26. The method of claim 25 further comprising identifying the protein based on a comparison between the reconstructed amino acid sequences from the nucleic acid records to a database or library of known protein sequences or the genome.

* * * * *

SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 1
atcgctgact                                                          10

<210> SEQ ID NO 2
<211> LENGTH: 13
<212> TYPE: PRT
<213> ORGANISM: Artificial Sequence
<220> FEATURE:
<223> OTHER INFORMATION: Synthetic polypeptide

```
<400> SEQUENCE: 2

Cys Gly Ala Lys Trp His Pro Met His Gly Ala Ala Cys
1               5                   10

<210> SEQ ID NO 3
<211> LENGTH: 79
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is deoxyuridine
<220> FEATURE:
<221> NAME/KEY: misc_feature
<222> LOCATION: (11)..(11)
<223> OTHER INFORMATION: n is deoxyuridine
<220> FEATURE:
<221> NAME/KEY: misc_feature
<222> LOCATION: (18)..(18)
<223> OTHER INFORMATION: n is deoxyuridine
<220> FEATURE:
<221> NAME/KEY: misc_feature
<222> LOCATION: (22)..(22)
<223> OTHER INFORMATION: n is deoxyuridine
<220> FEATURE:
<221> NAME/KEY: misc_feature
<222> LOCATION: (28)..(49)
<223> OTHER INFORMATION: n is a, c, or t
<220> FEATURE:
<221> NAME/KEY: misc_feature
<222> LOCATION: (65)..(65)
<223> OTHER INFORMATION: T is modified by biotin
<220> FEATURE:
<221> NAME/KEY: misc_feature
<222> LOCATION: (73)..(74)
<223> OTHER INFORMATION: Modified by Int Spacer 9

<400> SEQUENCE: 3
aaaaaancat nccccagcnta cnctcacnnn nnnnnnnnnn nnnnnnnnna ccggttcgct    60
ggttttccca gcgaccggt                                                 79
```